United States Patent
Mann et al.

(10) Patent No.: US 6,997,920 B2
(45) Date of Patent: Feb. 14, 2006

(54) EXTERNAL INFUSION DEVICE WITH REMOTE PROGRAMMING, BOLUS ESTIMATOR AND/OR VIBRATION ALARM CAPABILITIES

(75) Inventors: Alfred E. Mann, Beverly Hills, CA (US); James D. Causey, III, Simi Valley, CA (US); Alan Haubach, Carlsbad, CA (US); Luis J. Malave, Valencia, CA (US); John Livingston, Newport Beach, CA (US); Cliff Hague, Sherman Oaks, CA (US); Chad Srisathapat, Sun Valley, CA (US); Jay Yonemoto, Diamond Bar, CA (US); Deborah Ruppert, Los Angeles, CA (US); Dennis P. Bishop, Van Nuys, CA (US); Adrian Gut, Los Angeles, CA (US); Bob Murtfeldt, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 313 days.

(21) Appl. No.: 10/401,085

(22) Filed: Mar. 27, 2003

(65) Prior Publication Data

US 2003/0181851 A1 Sep. 25, 2003

Related U.S. Application Data

(62) Division of application No. 10/062,838, filed on Jan. 31, 2002, which is a division of application No. 09/466,006, filed on Dec. 17, 1999, now Pat. No. 6,551,276, which is a continuation of application No. 09/334,858, filed on Jun. 16, 1999, now Pat. No. 6,554,798.
(60) Provisional application No. 60/096,994, filed on Aug. 18, 1998.

(51) Int. Cl.
*A61K 9/22* (2006.01)
*A61M 1/00* (2006.01)
*G06F 17/00* (2006.01)

(52) U.S. Cl. ............... 604/890.1; 604/122; 700/90

(58) Field of Classification Search .............. 604/890.1, 604/65–67, 93.01, 131, 151–155, 174, 179, 604/207–211, 236–238, 246–250, 503–504, 604/506, 45, 122, 903; 128/903; 700/90, 700/231; 455/418–420, 41.2–41.3; 341/176; 340/5.61, 5.64
See application file for complete search history.

(56) References Cited

U.S. PATENT DOCUMENTS 3,631,847 A  1/1972  Hobbs, II
(Continued)

FOREIGN PATENT DOCUMENTS

DE  4329229  3/1995
(Continued)

OTHER PUBLICATIONS

"506 Insulin Pump User Guide"; MiniMed; pp. cover–108; Oct. 1994.
(Continued)

*Primary Examiner*—Loan H. Thanh
*Assistant Examiner*—Catherine S. Williams
(74) *Attorney, Agent, or Firm*—Medtronic MiniMed, Inc.

(57) ABSTRACT

An infusion system for infusing a liquid into a body includes an external infusion device and a remote commander. The external infusion device includes a housing, a receiver, a processor and an indication device. The receiver is coupled to the housing and for receiving remotely generated commands. The processor is coupled to the housing and the receiver to receive remotely generated commands and to control the external infusion device in accordance with the commands. The indication device indicates when a command has been received and indicates when the command is being utilized to control the external infusion device so that the external infusion device is capable of being concealed from view when being remotely commanded. The remote commander includes a commander housing, a keypad for transmitting commands, and a transmitter for transmitting commands to the receiver of the external infusion device.

44 Claims, 11 Drawing Sheets

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,392,849 A | 7/1983 | Petre et al. |
| 4,395,259 A | 7/1983 | Prestele et al. |
| 4,443,218 A | 4/1984 | DeCant, Jr. et al. |
| 4,469,481 A | 9/1984 | Kobayashi |
| 4,475,901 A | 10/1984 | Kraegen et al. |
| 4,494,950 A | 1/1985 | Fischell |
| 4,529,401 A * | 7/1985 | Leslie et al. ............... 604/131 |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. ............... 74/111 |
| 4,678,408 A | 7/1987 | Nason et al. ............... 417/410 |
| 4,685,903 A | 8/1987 | Cable et al. ............... 604/154 |
| 4,696,671 A | 9/1987 | Epstein et al. |
| 4,731,051 A | 3/1988 | Fischell |
| 4,731,726 A | 3/1988 | Allen, III |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,019,974 A | 5/1991 | Beckers |
| 5,034,004 A | 7/1991 | Crankshaw |
| 5,050,612 A | 9/1991 | Matsumura |
| 5,078,683 A | 1/1992 | Sancoff et al. |
| 5,080,653 A | 1/1992 | Voss et al. |
| 5,100,380 A | 3/1992 | Epstein et al. |
| 5,153,827 A | 10/1992 | Coutre et al. |
| 5,216,597 A | 6/1993 | Beckers |
| 5,266,013 A | 11/1993 | Aubert et al. |
| 5,307,263 A | 4/1994 | Brown |
| 5,317,506 A | 5/1994 | Coutre et al. |
| 5,319,363 A | 6/1994 | Welch et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,357,427 A | 10/1994 | Langen et al. |
| 5,364,346 A | 11/1994 | Schrezenmeir |
| 5,368,562 A | 11/1994 | Blomquist et al. |
| 5,370,622 A | 12/1994 | Livingston et al. |
| 5,376,070 A | 12/1994 | Purvis et al. |
| 5,429,602 A | 7/1995 | Hauser |
| 5,437,634 A * | 8/1995 | Amano ............... 604/65 |
| 5,464,392 A | 11/1995 | Epstein et al. |
| 5,472,317 A | 12/1995 | Field et al. |
| 5,478,211 A | 12/1995 | Dominiak et al. |
| 5,482,446 A | 1/1996 | Williamson et al. |
| 5,485,408 A | 1/1996 | Blomquist |
| 5,558,640 A | 9/1996 | Pfeiler et al. |
| 5,569,187 A | 10/1996 | Kaiser |
| 5,573,506 A | 11/1996 | Vasko |
| 5,582,593 A * | 12/1996 | Hultman ............... 604/65 |
| 5,584,814 A * | 12/1996 | Schuster et al. ............ 604/187 |
| 5,593,390 A | 1/1997 | Castellano et al. |
| 5,594,638 A | 1/1997 | Iliff |
| 5,609,060 A | 3/1997 | Dent |
| 5,609,575 A | 3/1997 | Larson et al. |
| 5,616,124 A * | 4/1997 | Hague et al. ............... 604/65 |
| 5,620,312 A | 4/1997 | Hyman et al. |
| 5,626,144 A | 5/1997 | Tacklind et al. |
| 5,630,710 A | 5/1997 | Tune et al. |
| 5,643,212 A | 7/1997 | Coutre et al. |
| 5,647,853 A | 7/1997 | Feldmann et al. |
| 5,660,176 A | 8/1997 | Iliff |
| 5,665,065 A | 9/1997 | Colman et al. |
| 5,681,285 A | 10/1997 | Ford et al. |
| 5,685,844 A | 11/1997 | Marttila |
| 5,687,734 A | 11/1997 | Dempsey et al. |
| 5,704,366 A | 1/1998 | Tacklind et al. |
| 5,764,159 A | 6/1998 | Neftel |
| 5,772,635 A | 6/1998 | Dastur et al. |
| 5,788,669 A | 8/1998 | Peterson |
| 5,807,336 A | 9/1998 | Russo et al. |
| 5,814,015 A | 9/1998 | Gargano et al. |
| 5,832,448 A | 11/1998 | Brown |
| 5,840,020 A | 11/1998 | Heinonen et al. |
| 5,840,026 A | 11/1998 | Uber, III et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,961,451 A | 10/1999 | Reber et al. |
| 5,997,476 A | 12/1999 | Brown |
| 6,009,339 A | 12/1999 | Bentsen et al. |
| 6,032,119 A | 2/2000 | Brown et al. |
| 6,101,478 A | 8/2000 | Brown |
| 6,142,008 A * | 11/2000 | Cole et al. ............... 73/19.03 |
| 6,171,276 B1 * | 1/2001 | Lippe et al. ............... 604/67 |
| 6,175,752 B1 | 1/2001 | Say et al. |
| 6,246,992 B1 | 6/2001 | Brown |
| 6,269,340 B1 | 7/2001 | Ford et al. |
| 6,551,276 B1 * | 4/2003 | Mann et al. ............... 604/131 |
| 6,554,798 B1 * | 4/2003 | Mann et al. ............... 604/131 |
| 6,556,963 B1 | 4/2003 | Tetzlaff |
| 2002/0107476 A1 * | 8/2002 | Mann et al. ............... 604/67 |
| 2003/0181851 A1 * | 9/2003 | Mann et al. ............... 604/65 |
| 2003/0181852 A1 * | 9/2003 | Mann et al. ............... 604/65 |
| 2003/0187525 A1 * | 10/2003 | Mann et al. ............... 700/90 |
| 2003/0191431 A1 * | 10/2003 | Mann et al. ............... 604/67 |
| 2003/0195462 A1 * | 10/2003 | Mann et al. ............... 604/67 |
| 2003/0212364 A1 * | 11/2003 | Mann et al. ............... 604/131 |

FOREIGN PATENT DOCUMENTS

| | | |
|---|---|---|
| EP | 0806738 | 11/1997 |
| EP | 0880936 | 12/1998 |
| GB | 2218831 | 11/1989 |
| WO | 9620745 | 7/1996 |
| WO | 9636389 | 11/1996 |
| WO | 9721456 | 6/1997 |
| WO | 9820439 | 5/1998 |
| WO | 9824358 | 6/1998 |
| WO | 9842407 | 10/1998 |
| WO | 9849659 | 11/1998 |
| WO | 9859487 | 12/1998 |
| WO | 9908183 | 2/1999 |
| WO | 9910801 | 3/1999 |
| WO | 9918532 | 4/1999 |
| WO | 9922236 | 5/1999 |

OTHER PUBLICATIONS

MiniMed Dosage Calculator Initial Meal Bolus Guidelines / MiniMed Dosage Calculator Intial Basal Rate Guidelines Percentage Method, MiniMed, 4 pages, 1994.

"Counting Carbohydrates How to Zero in on Good Control", Betty Page Brackenridge, MS, RD, CDE, et al., MiniMed Technologies Inc.; 12744 San Fernando Road, Sylmar, CA 91342; pp. cover page–23; 1995.

"The Insulin Pump Therapy Book" MiniMed Technologies; Insights from the Experts; Introduction by Jay S. Skyler, MD; Edited by Linda Fredrickson, MA, RN, CDE; pp. 1–192; 1995.

"507 Insulin Pump User's Guide"; MiniMed; pp. cover–127; May 1996.

"507C Insulin Pump User Guide"; MiniMed; pp. 1–132; Mar. 1998.

Teens Pumping it Up Insulin Pump Therapy Guide for Adolescents; $2^{nd}$ Edition; Supported by an Educational Grant from MiniMed; Elizabeth Boland, MSN, APRN, PNP, CDE; pp. iii–x; 1–47; Jul. 1998.

MiniMed® 507C Insulin Pump *For those who appreciate the difference brochure*; MiniMed® International, (Aug. 1998).

MiniMed® Insulin Pump Comparison brochure, (Oct. 1999).

MiniMed® 508 Flipchart Guide to Insulin Pump Therapy, (1999).

"Carbohydrate Counting A Primer for Insulin Pump Users to Zero in on Good Control", Karmeen Kulkarni, RD, MS, CDE, et al., MiniMed Inc., 12744 San Fernando Road, Sylmar, CA 91342; pp. Cover page–50, 1999.

MiniMed® Now I Can Correction Bolus Calculator / MiniMed® Now I Can Meal Bolus Calculator, (Jul. 2000).

MiniMed® Now I Can brochure, (Sep. 2000).

MiniMed® Now I Can MiniMed Diabetes Management packet, (Sep. 2000).

Medtronic MiniMed The 508 Insulin Pump A Tradition of Excellence brochure, (Feb. 2002).

"Medtronic MiniMed Meal Bolus Calculator and Correction Bolus Calculator" International Version; 2002.

Disetronic H–TRON® plus Reference Manual.

Disetronic H–TRON® plus Quick Start Manual.

MiniMed 506 Web Pages, (Nov. 11, 1996).

MiniMed 507 Web Pages—MiniMed 507 Specifications, (Jan. 24, 1997).

"Insulin Infusion Pump Therapy", Intensive Diabetes Management. (1995).

"Reduction in Severe Hypoglycemia with Long–Term Continuous Subcutaneous Insulin Infusion in Type I Diabetes", Diabetes Care. vol. 19. No. 4. (Apr. 1996).

"Carbohydrates Gram Counting: A Key to Accurate Mealtime Boluses in Intensive Diabetes Therapy", Practical Diabetology, vol. 11, No. 2, (Jun. 1992).

Voice of the Diabetic. vol. 11, No. 3, (Summer Edition 1996).

*Pumping Insulin: The Art of Using an Insulin Pump*, John Walsh, P.A. and Ruth Roberts, M.A., Published by MiniMed (1989).

MiniMed Web Pages, "FAQ: The Practical Things . . . ,", (Nov. 11, 1996).

MiniMed Web Pages, "Wanted: a Few Good Belt Clips!", (Jan. 24, 1997).

"Continuous Subcutaneous Insulin Infusion [CSII] External Devices: Current Status", Update in Drug Delivery Systems, Futura Publishing Company, (1989).

"Continuous Subcutaneous Insulin Infusion: A Review of the Past and Its Implementation for the Future", Diabetes Spectrum, vol. 7, No. 2, (Mar./Apr. 1994).

"Insulin Pump Therapy: Acceptable Alernative to Injection Therapy", Postgraduate Medicine, vol. 99, No. 3, (Mar. 1996).

"Initiation and Management of Insulin Pump Therapy", The Diabetes Educator, vol. 19, No. 1, (Jan./Feb. 1993).

"Intensive Insulin Therapy for Treatment of Type I Diabetes", Diabetes Care, vol. 13, No. 12, (Dec. 1990).

* cited by examiner

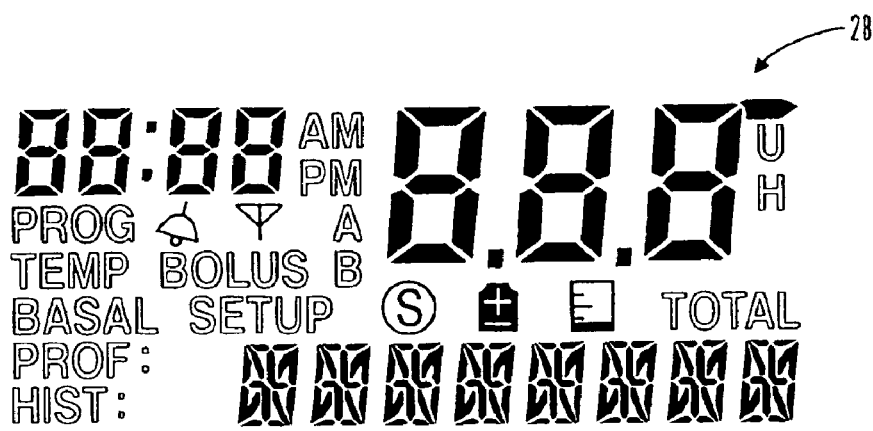

FIG. 5

| NO. | SETUP II MENU OPTIONS |
|---|---|
| 1 | VARIABLE BOLUS MODE ON/OFF SCREEN |
| 2 | BOLUS ESTIMATOR ON/OFF SCREEN |
| 3 | MAXIMUM BOLUS SCREEN |
| 4 | MAXIMUM BASAL SCREEN |
| 5 | ALARM REVIEW SCREEN |
| 6 | RF DEVICE ID SCREEN |
| 7 | AUDIO BOLUS MODE ON/OFF SCREEN |
| 8 | PERSONAL DELIVERY PATTERN SCREEN |
| 9 | ALARM MODE (AUDIO/VIBRATE) SCREEN |
| 10 | CHILD BLOCK ON/OFF SCREEN |
| 11 | TIME DISPLAY SCREEN |
| 12 | INSULIN CONCENTRATION SCREEN |
| 13 | SETUP I SCREEN |
| 14 | SETUP EXIT SCREEN |

FIG. 6

| NO. | MAIN MENU OPTIONS |
|---|---|
| 1 | TIME SCREEN |
| 2 | BOLUS & BOLUS HISTORY SCREEN |
| 3 | SUSPEND/RESUME PUMP SCREEN |
| 4 | BASAL RATE SCREEN |
| 5 | TEMP. BASAL RATE SCREEN |
| 6 | DAILY TOTALS REVIEW SCREEN |
| 7 | PRIME BOLUS SCREEN |
| 8 | SETUP I SCREEN |
| 9 | SETUP II SCREEN |

| PARAMETER | FACTORY DEFAULT |
|---|---|
| INSULIN CONCENTRATION | U100 |
| BASAL RATE PROFILES | PROFILE 1, 0.0 U/H (PERSONAL PATTERNS 2 AND 3 ARE ALSO SET TO PROFILE 1 OF 0.0 U/H). PERSONAL PATTERN 1 IS THE DEFAULT. |
| MAXIMUM MEAL BOLUS | 10.0 U |
| MAXIMUM BASAL RATE | 2.0 U/H |
| TIME | 12:00 AM, JAN 1, 1998 AT TIME OF PUMP POWER ON RESET (E-01) |
| TIME DISPLAY FORMAT | 12 HOUR (FOR U.S.A.), 24 HOUR (FOR EUROPE) |
| AUDIO BOLUS MODE | OFF |
| AUDIO BOLUS INCREMENT | 0.5 U (U100) |
| BEEP VOLUME | 2 (MEDIUM) |
| AUTOMATIC OFF DURATION | -- (DISABLED) |
| DAILY TOTALS | ALL 90 DAYS 0.0 U (USER CAN REVIEW LAST 7 ONLY) |
| BOLUS HISTORY | ALL 450 BOLUSES 0.0 U (USER CAN REVIEW LAST 24 ONLY) |
| PRIME BOLUS HISTORY | ALL 50 BOLUSES 0.0 U (USER CAN REVIEW LAST 9) |
| ALARM MODE | AUDIO |
| LOW VOLUME ALERT | OFF |
| ALARM CLOCK | OFF |
| CHILD LOCK | OFF |
| BOLUS ESTIMATOR | OFF |
| TARGET BLOOD GLUCOSE | 100 MG/DL |
| INSULIN SENSITIVITY | 30 |
| CARBOHYDRATE RATIO | 15 |
| EXCHANGE RATIO | 1.0 |
| BOLUS ESTIMATOR LOCKOUT | 1 HR |
| BLOOD GLUCOSE TIMER | OFF |
| RF-DEVICE | OFF |
| ALARM HISTORY | BLANKS (USER CAN REVIEW LAST 12 ONLY) |

FIG. 14

EXTERNAL INFUSION DEVICE WITH REMOTE PROGRAMMING, BOLUS ESTIMATOR AND/OR VIBRATION ALARM CAPABILITIES

RELATED APPLICATIONS

This is a divisional application of U.S. patent application Ser. No. 10/062,838 filed on Jan. 31, 2002, which is a divisional of U.S. patent application Ser. No. 09/466,006 filed on Dec. 17, 1999, now U.S. Pat. No. 6,551,276, which is a continuation application of U.S. patent application Ser. No. 09/334,858 filed Jun. 16, 1999, now U.S. Pat. No. 6,554,798, which claims priority on U.S. Provisional Patent Application Ser. No. 60/096,994 filed on Aug. 18, 1998 now expired, which is herein specifically incorporated by reference.

FIELD OF THE INVENTION

This invention relates to external infusion devices and, in particular embodiments, to a medication infusion device that includes the capability to be remotely controlled, a bolus estimator to determine the dosage to be administered by the infusion device, and a vibration alarm.

BACKGROUND OF THE INVENTION

Insulin must be provided to people with Type I and many with Type II diabetes. Traditionally, since it cannot be taken orally, insulin has been injected with a syringe. More recently, use of external infusion pump therapy has been increasing, especially for delivering insulin for diabetics using devices worn on a belt, in a pocket, or the like, with the insulin delivered via a catheter with a percutaneous needle or cannula placed in the subcutaneous tissue. For example, as of 1995, less than 5% of Type I diabetics in the United States were using pump therapy. There are now about 7% of the currently over 900,000 Type I diabetics in the U.S. using insulin pump therapy, and the percentage is now growing at an absolute rate of over 2% each year. Moreover, the number of Type I diabetics is growing at 3% or more per year. In addition, growing numbers of insulin using Type II diabetics are also using external insulin infusion pumps. Physicians have recognized that continuous infusion provides greater control of a diabetic's condition, and are also increasingly prescribing it for patients. In addition, medication pump therapy is becoming more important for the treatment and control of other medical conditions, such as pulmonary hypertension, HIV and cancer. Although offering control, pump therapy can suffer from several complications that make use of a pump less desirable for the user.

One drawback is the inability to conceal an external infusion pump and catheter tubing from view. Many users desire to hide the external pump under clothing so as not to seem different from normal people. However, this is inconvenient or impractical, especially for diseases such as diabetes, since a user must have ready access to the external pump for monitoring or administering extra amounts of medication (i.e., boluses during the course of the day). If a user has concealed the external pump, the user must partially undress or carefully maneuver the external pump to a location that permits access to the display and keypad.

A further drawback is the inability to limit the access of the user to certain capabilities. For instance, the user should have access to the keypad so that the user can change the values and parameters of daily pump operation. However, there may be certain parameters that the user should not have access to. This can be especially important, when the pump is being used by children or the elderly. However, if access is very limited, a user may even have to go to the factory and/or to the physician to have the parameters changed.

Another drawback for diabetic pump users, in particular, is the determination of the amount of bolus insulin to be delivered for a meal so as to avoid high blood sugars that would otherwise be caused by the meal. This can be a difficult calculation using formulas and approximations that have several variables that must be measured and calculated. Often, it is easier, but not the best for control, for the user to simply guess what they need rather than to calculate the actual amount of the bolus needed to adequately cover the carbohydrates being consumed. However, in worse case scenarios, guessing can lead to under or overdosing of medication, sometimes with dire consequences.

Another drawback to using an infusion pump, is the step of priming the external infusion pump to remove gas bubbles in the reservoir and/or tubing. The user must first manually shake the reservoir to move any bubbles to the distal end of the reservoir. Then the user must carefully expel the bubbles through the tubing. However, unless all bubbles are moved to the distal end of the reservoir, the user will have to expel a larger amount of medication, which can be wasteful, and very costly for special types of medications, such as those used in HIV and cancer treatment. Improved methods of priming the external infusion pump are needed.

SUMMARY OF THE DISCLOSURE

It is an object of an embodiment of the present invention to provide an improved external infusion device, which obviates for practical purposes, the above mentioned limitations.

According to an embodiment of the invention, an external infusion device for infusion of a liquid into a body includes a housing, a receiver, a processor and indication device. The receiver is coupled to the housing for receiving remotely generated commands. The processor is coupled to the housing and the receiver to receive remotely generated commands and to control the external infusion device in accordance with the commands. The indication device indicates when a command has been received and indicates when the command is being utilized to control the external infusion device. In this way, the external infusion device can be operated when concealed from view by being remotely commanded.

Further embodiments include a memory for storing programs, and the receiver is capable of receiving software updates and facilitating remote programming of external infusion device capabilities. In addition, the memory may store patient infusion history and pump activity. Also, the remotely generated commands may be capable of programming and activating an audio (or vibratory) bolus delivery of the liquid by the external infusion device, a temporary basal rate delivery of the liquid by the external infusion device, of suspending delivery of the liquid by the external infusion device, an extended bolus (such as a square wave bolus or profiled bolus) delivery of the liquid by the external infusion device, and a dual wave bolus delivery of the liquid by the external infusion device.

In particular embodiments, an infusion system for infusing a liquid into a body includes an external infusion device and a remote commander. The external infusion device includes a housing, a receiver, a processor and an indication device. The receiver is coupled to the housing for receiving remotely generated commands. The processor is coupled to the housing and the receiver to receive remotely generated commands to control the external infusion device in accordance with the commands. The indication device indicates when a command has been received and indicates when the command is being utilized to control the external infusion device so that the external infusion device is capable of being concealed from view when being remotely commanded. The remote commander includes a commander housing, a keypad for transmitting commands, and a transmitter for transmitting commands to the receiver of the external infusion device.

In particular embodiments, the remote commander is sized to fit on a key ring. Also, the remote commander may use RF frequencies, optical frequencies, IR frequencies, ultrasonic frequencies, magnetic effects, or the like, to transmit remote commands to the external infusion device. In addition, the remote commander is capable of providing remote commands at a distance greater than 1 inch. Furthermore, the processor of the external infusion device has a unique identification code, and the remote commander includes the capability to read and learn the unique identification code of the external infusion device. Alternatively, the user call program in the unique identification code. The remote commander and the external infusion device use a unique identification code to substantially avoid interference with other external infusion devices.

In still other embodiments, the remote commander includes a mode that permits physician controlled programming of specific capabilities of the external infusion device to the exclusion of the user, and the remote commander may also include a link to a computer to allow programming to initiate or alter available capabilities of the external infusion device. Also, the external infusion device may include a memory for storing programs, and the receiver is capable of receiving software updates and facilitating remote programming of external infusion device capabilities. In addition, the memory may store patient infusion history and pump activity. Finally, the remote commander may be capable of receiving data from another medical device and providing the received data to the external infusion device and/or remotely commanding and controlling another medical device. Other embodiments of the remote commander may also display the data.

In further preferred embodiments, an external infusion device for infusion of a liquid into a body includes a housing, a processor, a bolus estimator and an indication device. The bolus estimator used in conjunction with the processor and externally supplied values will estimate an amount of liquid to be infused based upon an estimate of a material to be taken in by the body. The indication device is used to indicate when an amount of fluid to be infused has been estimated. In addition, the bolus estimator includes the capability to estimate a correction bolus based upon a current characteristic value and a target characteristic value and/or a liquid sensitivity that is used to determine the amount of liquid to be infused so as to estimate the correction bolus. Further, embodiments of the bolus estimator include a lockout to prevent the calculation of a bolus for a predetermined period of time after a bolus has been estimated by the bolus estimator. Other embodiments include a duration factor to account for how long a previously infused amount of liquid will remain active in the body, and to adjust the estimate accordingly. In preferred embodiments, the liquid to be infused is insulin, and the material to be taken in is carbohydrates. Also, codes representing the carbohydrate levels of specific foods or meals may be used as the externally supplied values.

In yet another embodiment, an external infusion device for infusion of a liquid into a body includes a housing containing a reservoir, a processor and a vibration device. The processor is coupled to the housing. The vibration device is used in conjunction with the processor to provide an alarm, and to generate sufficient vibration to assist in removing gas bubbles from the fluid in the reservoir during priming of the external infusion device. In further embodiments, the vibration device is used to agitate the fluid in the reservoir in between periodic deliveries of the fluid by the external infusion device and/or during delivery of the fluid by the external infusion device.

In other embodiments, an external infusion device for infusion of a liquid into a body includes a housing containing a reservoir, a processor, an audible alarm and a vibration device. The processor is coupled to the housing, and the audible alarm. The vibration device is used in conjunction with the processor and the audible alarm to provide an alarm. In further embodiments, the vibration device is also used to agitate the fluid in the reservoir in between periodic deliveries of the fluid by the external infusion device and/or during delivery of the fluid by the external infusion device. In particular embodiments, the processor selects to activate one of the audible alarm and vibration alarm independently of the unselected alarm.

In still yet another embodiment, an external infusion device for infusion of a liquid into a body includes a housing, a processor, a keypad and an indication device. The processor is coupled to the housing, and the keypad is coupled to the housing and used in conjunction with the processor to determine an estimate of remaining battery power. The indication device indicates an estimate of remaining battery power.

In still further embodiments, an external infusion device for infusion of a liquid into a body includes a housing, a processor, a memory, a keypad and an indication device. The processor is coupled to the housing, and the memory is coupled to and used in conjunction with the processor to store at least two personal delivery patterns. The keypad is also coupled to the housing and used in conjunction with the processor to select one of the at least two personal delivery patterns, and the indication device indicates the selected personal delivery pattern. In preferred embodiments, the processor controls the external infusion device in accordance with the selected one of the at least two personal delivery patterns.

In further embodiments, an external infusion device for infusion of a liquid into a body includes a housing, a processor, a memory, a keypad and an indication device. The processor is coupled to the housing, and the memory is coupled to and used in conjunction with the processor to store at least two basal rate profiles. The keypad is also coupled to the housing and used in conjunction with the processor to program the at least two basal rate profiles, and the indication device indicates the basal rate profile during programming. In preferred embodiments, the processor controls the external infusion device in accordance with the programmed at least basal rate profiles.

In yet further embodiments, an external infusion device for infusion of a liquid into a body includes a housing, a processor, a memory, a keypad and an indication device. The processor is coupled to the housing, and the memory is coupled to and used in conjunction with the processor to store at least two bolus types. The keypad is also coupled to the housing and used in conjunction with the processor to select one of the at least two bolus types, and the indication device indicates the selected bolus type. In preferred embodiments, the processor controls the external infusion device in accordance with the selected one of the at least two bolus types.

In yet still further embodiments, an external infusion device for infusion of a liquid into a body includes a housing, a receiver, processor, memory and an indication device. The receiver is coupled to the housing for receiving remotely generated commands. The processor is coupled to the housing and the memory device. The memory is used in conjunction with the processor to store at least two personal delivery patterns, and the processor is coupled to the receiver to receive the remotely generated commands and to control the external infusion device in accordance with the commands to select one of the at least two personal delivery patterns. The indication device is used to indicate the selected personal delivery pattern and when a command has been received to control the external infusion device in accordance with the selected personal delivery pattern such that the external infusion device is capable of being concealed from view when being remotely commanded. Also, the processor controls the external infusion device in accordance with the selected one of the at least two personal delivery patterns.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 5 is a front plan view of an LCD display for use in an embodiment of the present invention.

FIG. 6 is a table of Setup II options used on external infusion devices in accordance with embodiments of the present invention.

FIG. 14 is a chart illustrating factory default setting used by embodiments of the present invention.

DETAILED DESCRIPTION OF THE PREFERRED EMBODIMENTS

Figure 1:
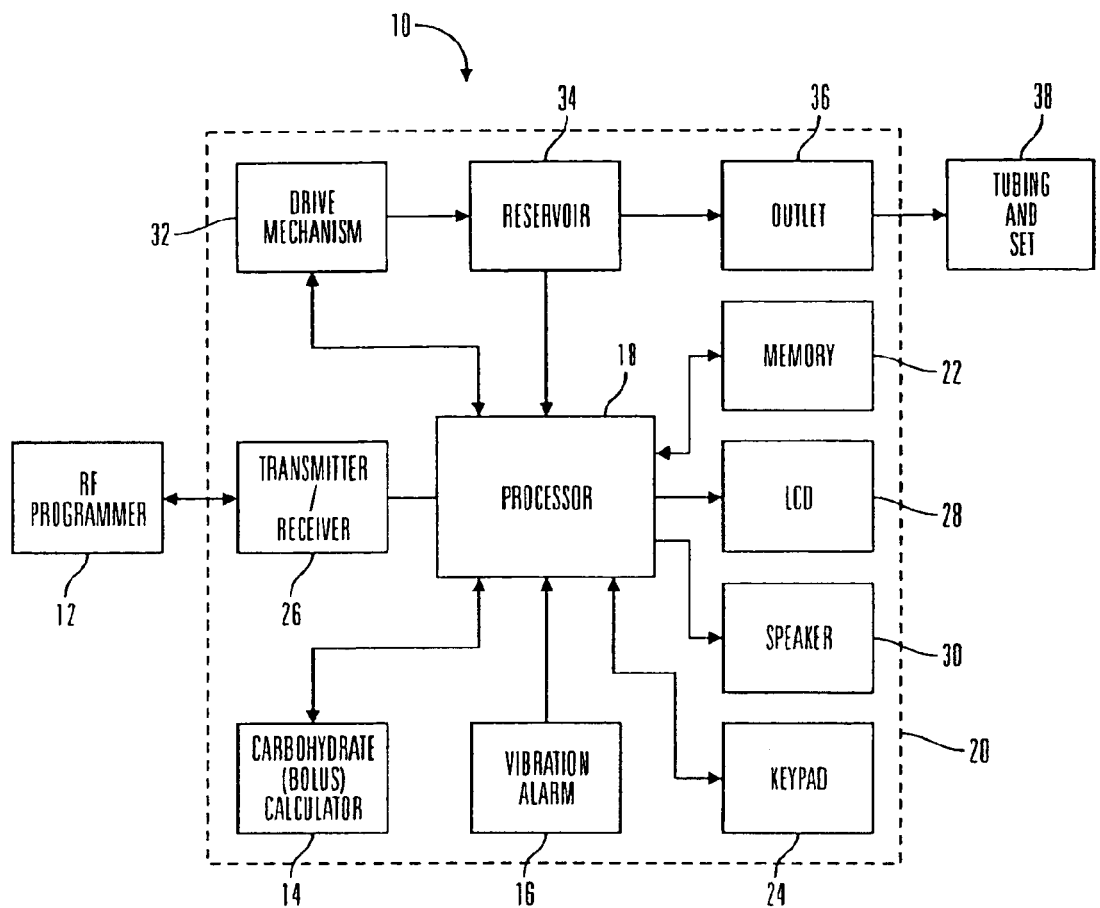
FIG. 1 is a simplified block diagram of an external infusion device and system in accordance with an embodiment of the present invention.

As shown in the drawings for purposes of illustration, the invention is embodied in an external infusion device for infusion of a liquid, such as medication, chemicals, enzymes, antigens, hormones, vitamins or the like, into a body of a user. In preferred embodiments to the present invention, the external infusion device is an external infusion pump, which includes an RF programming capability, a carbohydrate (or bolus) estimation capability and/or vibration alarm capability. Particular embodiments are directed towards use in humans; however, in alternative embodiments, the external infusion devices may be used in animals.

As illustrated in FIG. 1, preferred embodiments of the external infusion device 10 include a remote RF programmer 12, a carbohydrate (or bolus) estimator 14 and/or a vibration alarm 16. The RF programmer 12 and carbohydrate estimator 14 communicate with a processor 18 contained in a housing 20 of the external infusion device 10. The processor 18 is used to run programs and control the external infusion device 10, and is connected to an internal memory device 22 that stores programs, historical data, user defined information and parameters. In preferred embodiments, the memory device is a Flash memory and SRAM; however, in alternative embodiments, the memory device 22 may include other memory storage devices such as ROM, DRAM, RAM, EPROM, dynamic storage such as other flash memory, energy efficient hard-drive, or the like. In preferred embodiments, the external infusion device 10 is an external infusion pump that is programmed through a keypad 24 on the housing 20 or by commands received from the RF programmer 12 through a transmitter/receiver 26. Feedback from the external infusion device 10 on status or programming changes are displayed on an LCD 28 and/or audibly through a speaker 30. In alternative embodiments, the keypad 24 may be omitted and the LCD 28 may be used as a touch screen input device or the keypad 24 may utilize more keys or different key arrangements then those illustrated in the figures. The processor 18 is also coupled to a drive mechanism 32 that is connected to a fluid reservoir 34 containing fluid that is expelled through an outlet 36 in the reservoir 34 and housing 20, and then into a body of a user through tubing and a set 38. In further alternative embodiments, the keypad 24, LCD 20, speaker 24 may be omitted from the external infusion device, and all programming and data transfer is handled through the RF programmer 12.

Figure 2:
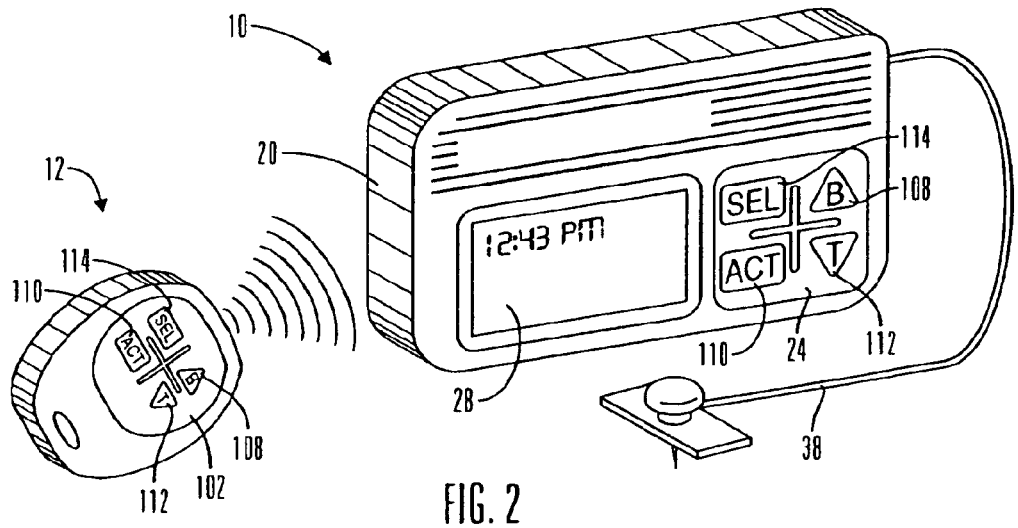
FIG. 2 is a perspective view of an external infusion device and system in accordance with an embodiment of the present invention.

Generally, as shown in FIG. 2, preferred embodiments of the external infusion device 10 are an external insulin pump having the capability to deliver 0 to 35 Units/hour in basal rates and up to 25.0 Units per meal bolus of U-100 Insulin. In alternative embodiments, the external pump delivers other concentrations of insulin, or other liquids, and may use other limits on the delivery rate.

The external infusion device 10 will also give the user the choice of an audible alarm and/or vibration alarm 16 such as of a warning that is indicative of a low reservoir situation or low battery or some malfunction of the system, such as an occlusion of the outlet that restricts the delivery of the fluid. Alarms may start out at a low level and escalate until acknowledged by the user. In further embodiments, both an audible alarm and a vibration alarm may be given at the same time.

As shown in FIG. 5, embodiments of the external infusion device 10 will utilize a segmented screen LCD 28 that offers multiple-language capability in approximately 6 languages. However, alternative embodiments may include larger or smaller language capabilities. Further alternative embodiments, may utilize an LCD that uses a dot matrix, active matrix, or the like. A scratch resistant window may be utilized to provide improved durability, better viewing and less glare.

Figure 15:
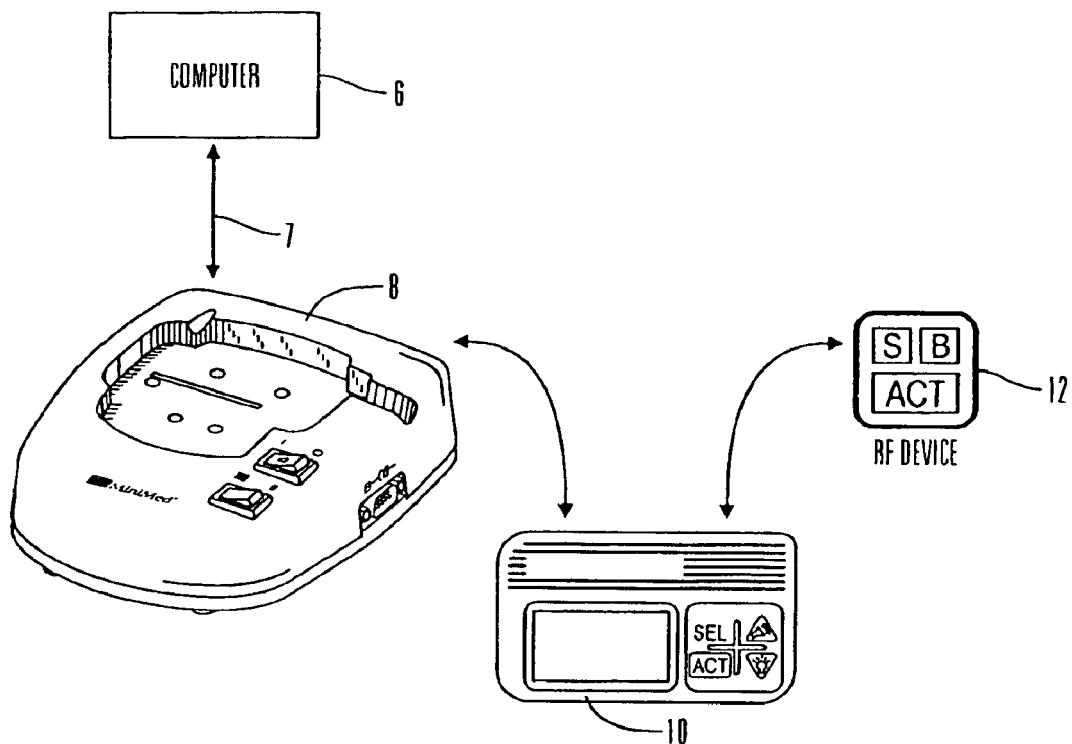
FIG. 15 is a simplified diagram of an external infusion device and system in accordance with another embodiment of the present invention.

Several programming options will be available in the external infusion device 10, and will include at least two customized basal profiles, a carbohydrate (or bolus) estimator 14 and an alarm clock, as well as remote and on-device programming. Additionally, a physician/educator will be able to configure the external infusion device 10 through a Communications Station (Communication-Station—shown in FIG. 15) to provide or restrict access to certain programming options. Particular embodiments of the external infusion device 10 will also download stored information through the Communication-Station. Further description of a Communication Station of this general type is be found in U.S. Pat. No. 5,376,070 to Purvis et al., entitled DATA TRANSFER SYSTEM FOR AN INFUSION PUMP, which is herein incorporated by reference. This information can be used alone or combined with information from a Glucose Meter and/or a Glucose Sensor (not shown) to assist the user and/or the health care professional in making intelligent therapy decisions. Moreover, the information, programs and data may be downloaded to a remote or local PC, laptop, Communication-Station, or the like, for analysis and review by a MiniMed or a trained health care professional through the transmitter/receiver 26. The data may also be downloaded through a Communication-Station 8 to a remotely located computer 6 such as a PC, laptop, or the like, over communication lines 7, by modem or wireless connection, as shown in FIG. 15.

The external infusion device 10 will also have additional memory capacity to allow configuring of the display during manufacturing to display information in several different foreign languages, and allow for future upgrades and revisions without the requirement of a hardware change. For example, a PC program will enable manufacturing to select the language for the pump. Languages are contingent upon available space, but will include English, French, Spanish, Italian, Dutch, Swedish and German. In alternative embodiments, other languages will be determined based upon space availability.

RF Programmer

The remote RF programmer 12 (or remote commander) will enable the user to perform basic external infusion device 10 programming steps without accessing the keyboard 24 on the external infusion device 10 or looking at the LCD (Liquid Crystal Display) 28 screen. This will benefit visually impaired users of the external infusion device 10, since the remote RF programmer 12 will give them ready access to the most commonly used operations of the external infusion device 10, and will obviate the need for visual feedback. Of particular importance to the sight impaired will be the auditory feedback (and/or vibration feedback as discussed below) that the external infusion device 10 will provide. The instructions from the RF programmer 12 will be confirmed by a series of audible beeps (or if requested by programming, vibration) from the external infusion device 10. In alternative embodiments, the RF programmer 12 may include a receiver and provide an audio (or vibration) indication that the commands have been received and acknowledged by the external infusion device 10. In further embodiments, the keypad 102 on the remote RF programmer 12 will have the letters defining the capability of the key encoded in Braille, and the ridges that orient the user to the keypad 102 will be quite pronounced to assist in guiding the user to the proper function key. Other embodiments may utilize keys that have different sizes or shapes to further enhance the ability for users to identify the correct buttons to activate the various features and functions.

A remote RF programmer 12 will provide convenience and discretion for the user of the external infusion device 10 by allowing concealment of the external infusion device 10 under clothes, in pouches, or the like. Preferably, the RF programmer 12 is an optional accessory item on the external infusion device 10, and the external infusion device 10 will be fully functional without the use of the RF programmer 12. However, in alternative embodiments, the keypad 24 in the external infusion device 10 may be omitted and all programming would be handled by a local or remote PC, laptop, Communication-Station, RF programmer or the like. In preferred embodiments, the RF programmer 12 will also provide the user with the ability to perform the following functions: deliver a bolus, suspend/restart the external infusion device, and set and cancel a temporary basal rate. However, in alternative embodiments, the RF programmer may include still additional capabilities such as data transfer (e.g., external infusion device history data or data from other medical devices), updates to software and programming, or the like. In preferred embodiments, the data transfer capabilities between the RF programmer 12 and the transmitter/receiver 26 of the external infusion device 10 are two-way. In alternative embodiments, the data transfer from the RF programmer 12 to the external infusion device 10 is one-way, such that the RF programmer 12 does not receive transmissions from the external infusion device 10. In further embodiments, the RF programmer acts as a relay, or shuttle, for data transmission between the external infusion device 10 and a PC, laptop, Communication-station, or the like.

Figure 16:
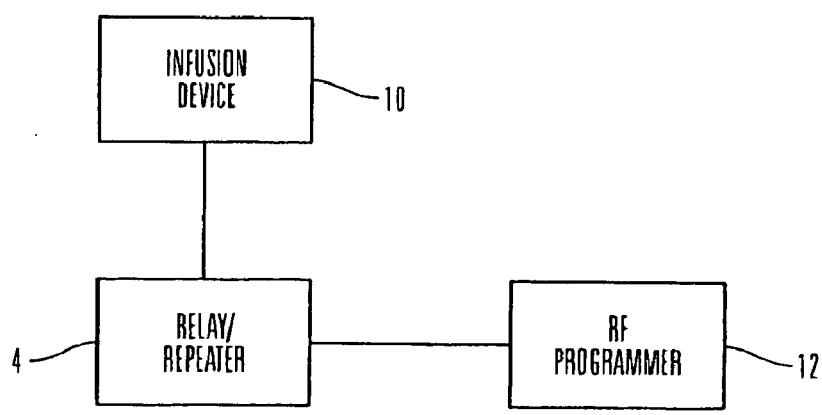
FIG. 16 is a simplified block diagram of an external infusion device and system in accordance with still another embodiment of the present invention.
Figure 17:
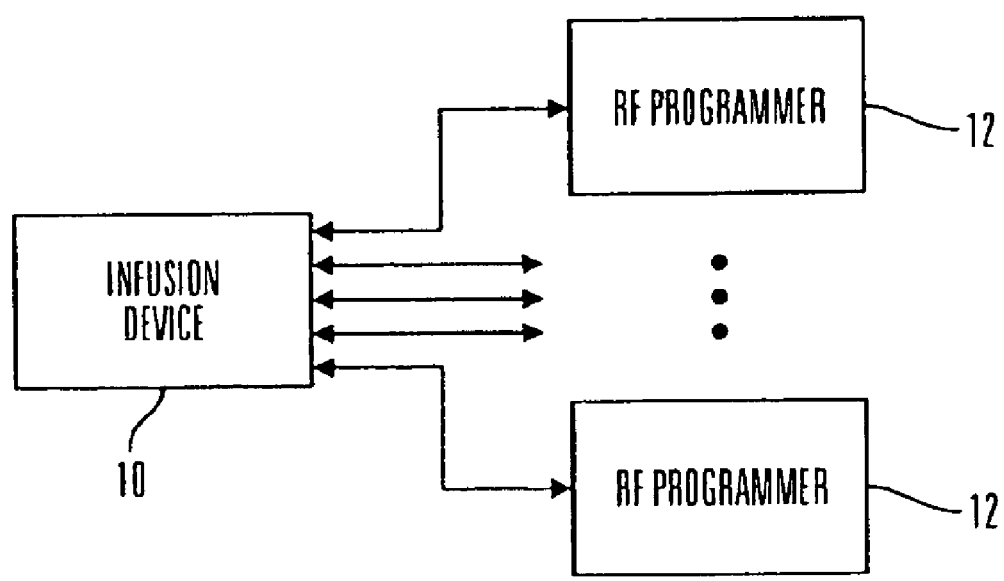
FIG. 17 is a simplified block diagram of an external infusion device and system in accordance with yet another embodiment of the present invention.

In addition, as shown in FIG. 16, a relay or repeater 4 may be used with an external infusion device 10 and an RF programmer 12 to increase the distance from which the RF programmer 12 can be used with the external infusion device 10. For example, the relay could be used to provide information to parents of children using the external infusion device 10 and allow them to program the external infusion device 10 from a distance with the RF programmer 12. The information could be used when children are in another room during sleep or doing activities in a location remote from the parents. In further embodiments, the relay 4 can include the capability to sound an alarm. In addition, the relay 4 may be capable of providing external infusion device 10 information to a remotely located individual via a modem connected to the relay 4 for display on a monitor, pager or the like. In a still further embodiment of the present invention, the external infusion device 10 is capable of being programmed by multiple RF programmers 12, as shown in FIG. 17. For instance, each RF programmer 12 would learn (or be programmed with) the unique code (discussed below) of the external infusion device 10. This would be useful for users that desired to have multiple RF programmers 12, such as at home, office and/or school or needed a replacement for an RF programmer that was lost.

Figure 3:
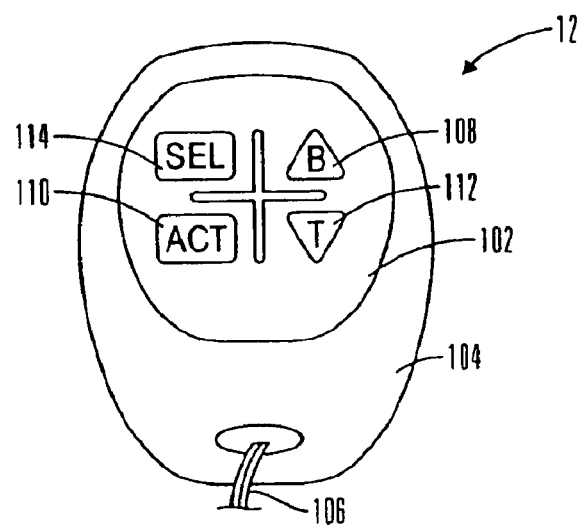
FIG. 3 is a top perspective view of an RF programmer in accordance with an embodiment of the present invention.

In preferred embodiments, the RF programmer 12 is similar in appearance to the type of remote that is used to lock and unlock car doors. It will have four (4) keys on a keypad 102 on a housing 104, which will be laid out in a square grid pattern, similar in appearance and layout to the keypad 24 on the external infusion device 10, as shown in FIGS. 2 and 3. In alternative embodiments, fewer keys may be used to simplify the RF programmer 12 (see FIG. 15), reduce manufacturing costs and/or to reduce the number of program capabilities available (such as Suspend (S), bolus (B), or the like). Preferably, the RF programmer 12 should include a ring 106 that fits on a key ring to lessen the likelihood that it might be lost. It should also have a "quick release" feature to allow the user to disconnect it from the key ring. Preferably, the RF programmer 12 is less than 1 cubic inch in volume; although larger or smaller volumes may be used. Preferred embodiments utilize RF frequencies; however, alternative embodiments, may use optical, infrared (IR), ultrasonic frequencies, magnetic effects, or the like, to communicate with the external infusion device 10.

Figure 4:
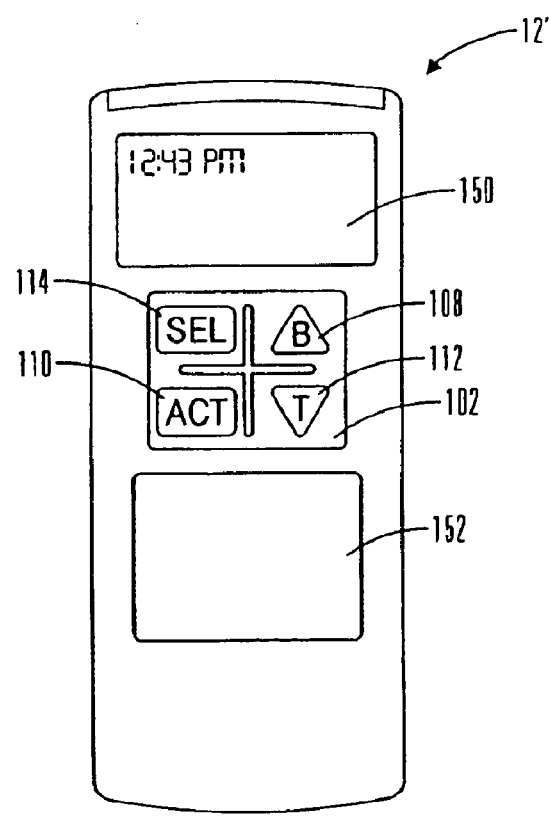
FIG. 4 is a top perspective view of a remote commander in accordance with another embodiment of the present invention.
Figure 7:
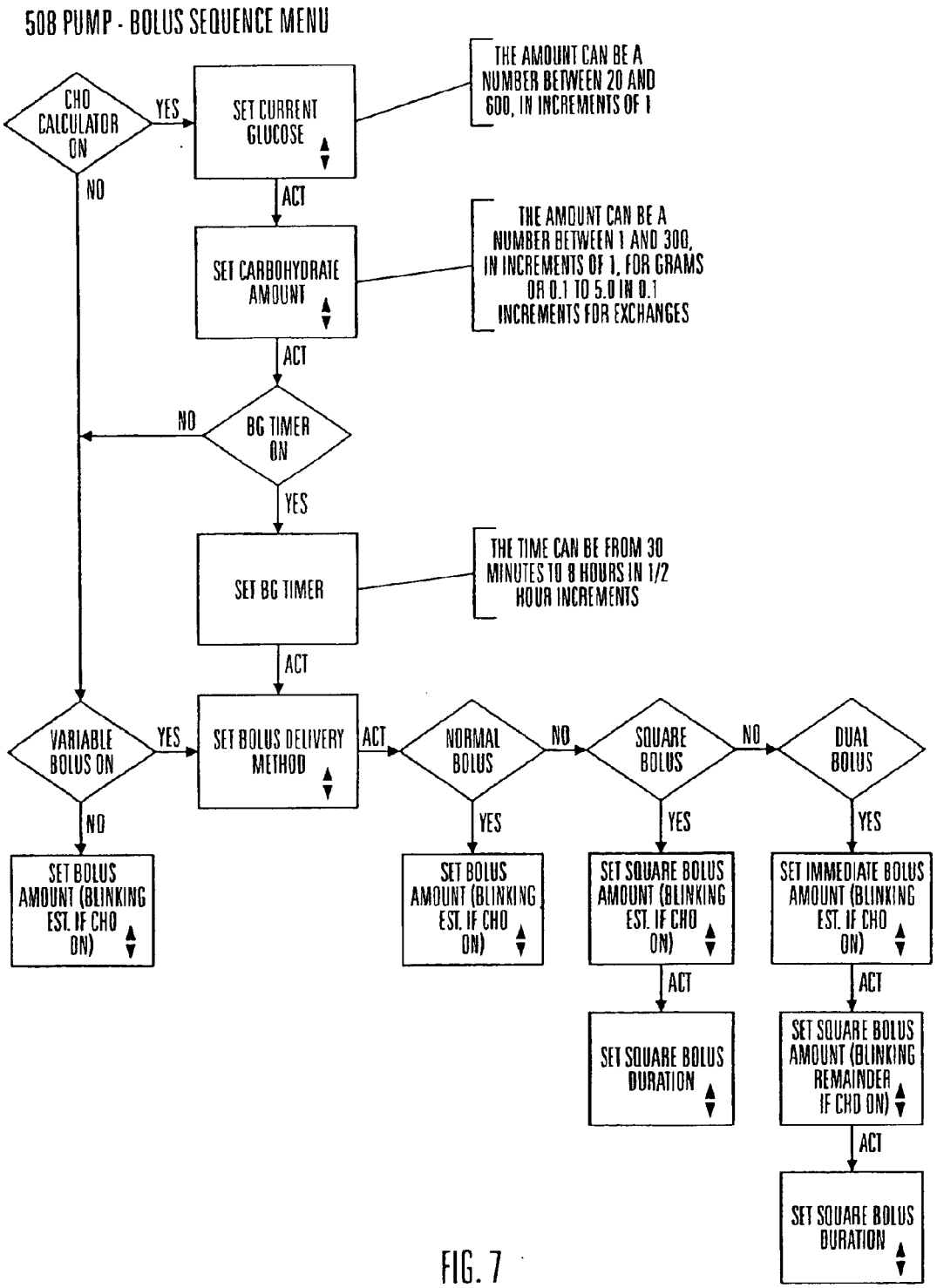
FIG. 7 is a flow diagram illustrating the steps used to set a bolus with and without the carbohydrate estimator in accordance with embodiments of the present invention.

Alternative embodiments of the RF programmer (controller or commander) 12', as shown in FIG. 4, may have more complex keypad arrangements 152, and may include a display device 150, such as an LCD, LED, plasma screen, or the like, to assist in programming the external infusion device 10. Further alternatives may include a microphone (not shown) and related circuitry to allow voice activated control of the external infusion device. In further alternative embodiments, the RF programmer 12' may be formed in larger sizes, comparable to a TV controller or a pocket calculator, and may include a display to facilitate more complicated or easier programming. Still further embodiments, may include the ability to receive data and information from the external infusion device 10 and/or a glucose monitoring device, and the ability to relay the information to another medical device, external infusion device 10, glucose monitor device, PC, laptop, Communication-Station, or the like. Data transmission may be to other devices or include the capability to receive data or instructions. An RF activation capability may be included in addition to the programming capability.

Each RF programmer 12 will include the capability to "learn" the unique code of the external infusion device 10 for which it is intended to be used. In one embodiment, the user will perform the following steps to learn the unique code: 1) remove the battery from the RF, programmer 12; 2) wait a few seconds and then replace the battery in the battery compartment; 3) press and hold the ACT key 110 on the remote keypad 102 (preferably, the remote will confirm that it has been activated with a long audible beep); and then the remote is held within approximately 12" to 18" (alternatively larger or smaller distances may be used) of the external infusion device 10 to receive the unique code from the transmitter/receiver 26 of the external infusion device 10. The RF programmer 12 will confirm successful learning of the unique code with audible beeps and/or vibration from the external infusion device 10 and/or RF programmer 12. In alternative embodiments, the user may manually enter or scan in the unique code identifying the RF programmer. In further alternative embodiments, the RF programmer 12 may also transmit a unique identification code that uniquely identifies the RF programmer 12 to the external infusion device 10 so that the external infusion device 10 will only accept commands from a particular RF programmer 12. In other embodiments, the unique code includes the serial number of the device to prevent confusion with other devices. In particular embodiments, the RF programmer 12 transmits commands to the infusion device 10, but does not include a receiver to receive back data from the infusion device 10. In this embodiment, the infusion device 10 includes the ability to store 3 unique codes to permit the infusion device 10 to be programmed by up to 3 different RF programmers 12. In other embodiments, the infusion device 10 may include more or less storage locations to permit programming of the infusion device 10 with a corresponding more or less number of RF programmers 12.

In preferred embodiments, the external infusion device 10 includes a receiver to receive the commands from the RF programmer 12. Normally, the receiver is in a standby mode (e.g., not receiving) and becomes active for short periods every 2.5 seconds (approximately) to see if there is any RF activity from the RF programmer 12. In alternative embodiments, the receiver of the external infusion device 10 may be on continuously or may become active more often or less often, with the selection being dependent on power capacity, expected frequency of use of the RF programmer 12, or the like. Generally, the receiver of the external infusion device 10 requires that the RF programmer send an activating message for a period lasting about 5 seconds for the RF programmer to be recognized by the receiver. In alternative embodiments, longer or shorter periods of time for sending the activating message may be used.

Once the receiver recognizes that there is a valid RF programmer 12 sending a message to the external infusion device 10 (i.e., with this device 10's unique code), the receiver will remain in an active mode until a complete sequence of commands has been received, or until the receiver times out due to a lack of RF communications from the RF programmer 12. Preferably, upon recognition of a valid RF programmer 12 trying to communicate with the receiver, the external infusion device 10 will activate its audio beeper (or its vibrator or the like) to let the user know that the external infusion device 10 has been activated by the RF programmer 12. Typically, the receiver of the infusion device 10 expects to receive a message with a valid preamble and message type, a recognized unique code, a valid function code (e.g., activate, bolus, suspend, or the like), an appropriate message count used by the receiver for reduction of RF interference problems, and a valid CRC on the transmitted message to ensure message integrity. Alternative embodiments, may include different message contents or components.

In operation, as discussed above, the RF programmer 12 may be used to program several capabilities, such as an audio (or vibration) bolus, a suspension of external infusion device operation, a temporary basal rate, an extended bolus (such as square wave, ramp, triangular or the like) or dual wave bolus. In addition, the user may program a profiled bolus that uniquely matches the needs of the individual user (for instance it may contain square, ramp, pulse or curved portions that make up the profile to be delivered over a period of time). It should be noted that the capabilities may also be directly programmed on the external infusion device 10 using the same sequence on the keypad of the external infusion device 10. The following are examples of how the various capabilities can be programmed using the keypad 102 on the RF programmer 12 (or similarly with the keypad 24 on the external infusion device 10).

EXAMPLE I

RF Programmed Audio Bolus

To deliver an audio bolus with the RF programmer 12, the user will press the "B" or Up arrow key (▲) 108 in the upper right hand corner of the RF programmer 12 keypad 102. Each time the Up arrow key (▲) 108 is pushed the amount of the audio bolus will increment in either 0.5 units or 1.0 units (depending on what the user programmed as the incremental step on the "audio" screen of the Set-up I menu—alternative embodiments may use other increments). In these examples, units are an increment of insulin. However, alternative embodiments, may define units to be any fluid volume, such as micro-liters, ccs, or the like, with the volume being dependent on the type of fluid to be infused. If the user exceeds the desired setting he can wait for an error signal, such as a "raspberry" type sound, buzzing, vibration, or the like, and then press the Up arrow key (▲) 108 on the RF programmer 12 to begin the process again.

When the desired audio bolus amount is programmed, the user presses the "activate" or ACT key 110 in the lower left corner of the keypad 102 on the RF programmer 12. The external infusion device 10 will then confirm the audio bolus amount with a series of audible beeps. In alternative embodiments, vibration may be used instead of or in addition to audible beeps. To deliver the audio bolus, the user will then press the ACT key 110 again to start delivery of the bolus. Alternatively, the external infusion device 10 may provide an audible indication by speech. In further alternative embodiments, the RF programmer 12' will have a display 150 and will provide a visual confirmation with or without an audio confirmation.

Counting the bolus increments will be facilitated by varying the audio tones for beeps that accompany the Up arrow key (▲) 108 presses. Four notes belonging to a musical chord will be used in repeating sequence as the Up arrow key (▲) 108 is repeatedly pressed to select a desired bolus amount. In alternative embodiments, more or fewer notes (and/or vibration) may be used. For example, if 0.5U (U-100) is the bolus increment, the first key press of the Up arrow key (▲) 108 will set the external infusion device 10 and LCD 28 to 0.5 U, and it will be accompanied by the first note in a chord. The second key press of the Up arrow key (▲) 108 will increment the external infusion device and the LCD 28 to 1.0 U, and it will be accompanied by the second note in the chord. The third key press of the Up arrow key (▲) 108 will increment the external infusion device 10 and LCD 28 to 1.5 U, and it will be accompanied by the third note in the chord. The fourth key press of the Up arrow key (▲) 108 will increment the external infusion device 10 and the LCD 28 to 2.0 U, and it will also be accompanied by the fourth note in the chord. On the fifth key press of the Up arrow key (▲) 108, the displayed bolus amount will be incremented again and the audio sequence will repeat in the same manner as just described.

When the desired bolus amount is displayed and/or sounded, the user continues by pressing the ACT key 110. The external infusion device 10 will play back the beep sequence generated during the bolus amount selection. The bolus delivery will commence after the user confirms the bolus amount selection by pressing the ACT key 110 once again. To cancel this bolus before it starts, the user may either allow the external infusion device 10 to time out and return to the time display or press the Down arrow key (▼) 112. Either of these will be accompanied by a "raspberry" type beep (and/or vibration) indicating the bolus has been cleared. Preferably, a standard time-out delay of 15 seconds applies to all keypresses involved during the bolus amount selection, but other time periods may be used.

Preferably, a BOLUS element, the word DELIVERY, and the updated amount delivered will be displayed on the LCD 28 while delivery is in progress. The external infusion device 10 will beep once at the end of the dose. In alternative embodiments, audible indications may be provided, such as beeps, chords, speech, or the like, and/or vibration.

EXAMPLE II

RF Programmed Suspension of External Infusion Device Operation

To temporarily suspend the operation of the external infusion device 10, the user will press the "select" or SEL key 114 in the upper left hand corner of the keypad 102 of the remote RF programmer 12, and then press the ACT key 10. The external infusion device 10 will confirm that it is in suspend mode with three (3) audible beeps (although different numbers of beeps and/or vibration may be used). In preferred embodiments, when the external infusion device 10 is in suspend mode, the LCD 28 will show "-S-", the word "STOPPED", and the time that the external infusion device 10 was placed in the suspend mode. When in the suspend mode, there is no drug delivery (either basal rate, or meal boluses). Preferably, the external infusion device 10 will beep an alert tone (and/or vibrate) every half hour to indicate that delivery has stopped. In alternative embodiments, other time periods may be used, or the alert tone may be omitted.

To restart the external infusion device 10, the user will again press the SEL key 114 and then presses the ACT key 110. The external infusion device 10 will beep once (and/or vibrate) to confirm the restart and then resume normal basal delivery and infusion device 10 operation. Alternatively, the external infusion device 10 may provide an audible indication by speech. In further alternative embodiments, the RF programmer 12' will have a display 150 and will provide a visual confirmation of the status of the external infusion device 10, with or without an audio confirmation.

EXAMPLE III

RF Programmed Temporary Basal Rate

A temporary basal rate, or basal override rate, is a rate that is delivered in lieu of a programmed, user defined profile segment rate that is generally delivered during this time period. The temporary basal rate is programmed with a rate and a duration.

To set a temporary basal rate, the user will press the "T" or Down arrow key (▼) 112 in the lower right hand corner of the keypad 102 on the RF programmer 12. Each press of the Down arrow key (▼) 112 will increment the duration of the temporary basal rate by 30 minutes. Counting the temporary basal rate duration increments will be facilitated by varying the audio tones for beeps that accompany the Down arrow key (▼) 112 presses. Four notes belonging to a musical chord will be used in repeating sequence as Down arrow key (▼) 112 is repeatedly pressed to select a desired duration of the basal rate. In alternative embodiments, more or fewer notes (and/or vibration) may be used. The temporary basal duration may be programmed from 30 minutes to 24 hours in half-hour increments. In alternative embodiments, other time periods may be used. In preferred embodiments, the tone of the beeps for a temporary basal rate may be distinctly different from a tone for incrementing a bolus. In alternative embodiments, different vibration may be used instead or in addition to the different audible beeps. If the user exceeds the desired setting, they can wait for an error signal, such as a "raspberry", buzzing, vibration, or the like, and then press the Down arrow (▼) 112 to begin the process again.

When the desired temporary basal rate duration has been set, the user will press the ACT key 110. The external infusion device 10 will confirm the duration of the temporary bolus rate with a series of audible beeps (and/or vibration). The user will then press the ACT key 110 again to confirm and accept the duration of the temporary basal rate. If the ACT key 110 is not pushed to confirm the amount, the external infusion device 10 will emit an audible error signal such as a "raspberry", buzzing, vibration, or the like. Alternatively, the external infusion device 10 may provide an audible indication by speech. In further alternative embodiments, the RF programmer 12' will have a display 150 and will provide visual confirmation of the temporary basal rate duration, with or without an audio confirmation.

To set the amount of the temporary basal rate, the user will press the Down arrow key (▼) 112 again. Each press of the Down arrow key (▼) 112 will increment the amount of the temporary basal by 0.1 units. Counting the amount temporary basal rate increments will be facilitated by varying the audio tones for beeps that accompany the Down arrow key (▼) 112 presses. Four notes belonging to a musical chord will be used in repeating sequence as Down arrow key (▼) 112 is repeatedly pressed to select a desired amount of the temporary basal rate. In alternative embodiments, more or fewer notes (and/or vibration) may be used. In these examples, units are an increment of insulin. However, alternative embodiments may define units to be any fluid volume, such as micro-liters, ccs, or the like, with the volume being dependent on the type of fluid to be infused. The rate may be set to a value from 0.0 U to the maximum programmable value of the basal rate. In alternative embodiments, different increments may be used. Preferably, the tone of these beeps (and/or vibration) will be distinctly different than the tone (and/or vibration) for setting the duration of the temporary basal rate. Once the desired amount has been set, the user will press the ACT key 110. The external infusion device 10 will confirm the amount of the temporary basal rate with a series of audible beeps (and/or vibration). The user will then press the ACT key 110 again to confirm and accept the amount of the temporary basal rate. If the ACT key 110 is not pushed to confirm the amount, the external infusion device 10 will emit an audible error signal, such as "raspberry", buzzing, vibration, or the like. Three short beeps (an/or vibration) every 30 minutes will confirm that the temporary basal rate is active. Alternatively, the external infusion device 10 may provide an audible indication by speech. In further alternative embodiments, the RF programmer 12' will have a display 150 and will provide visual confirmation of the temporary basal rate, with or without an audio confirmation.

To cancel a programmed temporary basal rate at any time during its intended operation, and resume the normal programmed basal rate, the user presses the Down arrow key (▼) 112 and then presses the SEL key 114 on the keypad 102 of the RF programmer 12. If a temporary basal rate had time remaining, the user will hear a long beep (and/or vibrate) to confirm that the temporary basal has been canceled. Otherwise, if no time was remaining, the user hears an error signal such as a "raspberry", buzzing, vibration, or the like, indicating that there was no time remaining on the temporary basal rate. Alternatively, the external infusion device 10 may provide an audible indication by speech. In further alternative embodiments, the RF programmer 12' will have a display 150 and will provide visual confirmation of the temporary basal rate, with or without an audio confirmation.

EXAMPLE IV

RF Programmed Extended Bolus

An extended bolus (such as a square wave bolus, ramp bolus, triangular bolus, profiled bolus or the like) is a bolus that is delivered over an extended period of time; rather, than all being delivered at once. To program an extended bolus with the RF programmer 12, the user will need access to the display LCD 28 of the external infusion device or perform the programming in two separate steps. Alternatively, an RF programmer 12' having a built in display 150 may be used.

To set an extended bolus, the user will set the duration of the extended bolus in the same manner that they set the duration for a Temporary Basal Rate. This involves using the Down arrow key (▼) 112 in the lower right corner of the keypad of the RF programmer 12, in the same manner as described above. The user will also select the type of extended bolus such as a square wave bolus, ramp bolus, triangular bolus, profiled bolus, or the like, to be delivered by previous selection of the type of extended bolus in the setup mode or by using an RF programmer in conjunction with a display. The remainder of the example demonstrates setting a square wave bolus.

When the ACT key 110 is pressed while a desired bolus amount is displayed, the bolus duration will be displayed on the LCD 28. The default bolus duration can be 30, 60 or 90 minutes, depending on the largest basal value of current setting and the desired bolus amount. The duration may be scrolled by using the Up arrow key (▲) 108 and the Down arrow key (▼) 112 on the keypad 102 of the RF programmer 12. Pressing the Up arrow key (▲) 108 will cause the duration to scroll in increments of 30 minutes up to 8 hours (the preferred maximum duration—although other durations or increments may be used), at which point it will wrap around to minimum duration. Pressing the Down arrow key (▼) 112 will cause the duration to wrap around to 8 hours, then scroll down in increments of 30 minutes. In further embodiments, the use of the Down arrow (▼) 112 will always stop at zero to avoid a wrap-around or require one or more additional depressions (possibly accompanied by a beep and/or vibration) to warn a user that they are now at the maximum value. Alternatively, the RF programmer 12' may include different additional keys (such as 152 in FIG. 4) that can be used to implement the square wave bolus, or a selectable menu on the RF programmer 12'.

Next, to set the amount of the square wave bolus, the user will press the Up arrow key (▲) 108 in the upper right hand corner of the keypad 102 of the RF programmer 12. Each depression will enable incrementing the amount of the square wave bolus in 0.1 unit increments; although other increments may be used. The external infusion device 10 will give a distinct auditory (and/or vibrating) confirmation of the selected bolus amount. The square wave will not be implemented until the user presses the ACT key 110 to accept the selected amount. Preferably, the external infusion device 10 provides confirmation by an audible beep (and/or vibration). Alternatively, the external infusion device 10 may provide an audible indication by speech. In further alternative embodiments, the RF programmer 12' will have a display 152 and will provide visual confirmation of the square wave bolus, with or without an audio confirmation.

To enhance flexibility, preferred embodiments of the external infusion device 10 will enable the user to deliver a normal bolus during a programmed Square Wave. Once the normal bolus has been delivered, the square wave will resume operation until completed.

EXAMPLE V

RF Programmed Dual Wave Bolus

A dual wave bolus is a combination of a normal (or immediately given) bolus with a square wave bolus. To program a dual wave bolus with the RF programmer 12, the user will need access to the display LCD 28 of the external infusion device or perform the programming in two separate steps. Alternatively, an RF programmer 12' having a built in display 150 may be used.

To set a dual wave bolus, the user will press the ACT key 110 on the bolus history screen. The word "NORMAL" will start to blink on the LCD 28 and/or provide an audible (and/or vibration) indication. The user can press the Up arrow key (▲) 108 or Down arrow key (▼) 112 to choose the type of bolus desired. By pressing the ACT key 110, while the LCD 28 of the external infusion device 10 blinks the word "DUAL" (and/or provides an audible indication), a dual bolus is chosen. The LCD 28 of the external infusion device 10 will show the word "NOW" and/or the dashes for the normal bolus portion amount will blink on the LCD 28 (and/or an audible and/or vibration indication is provided). The user can then select a bolus amount for the "informal" bolus portion using the Up arrow key (▲) 108 or Down arrow key (▼) 112, and then press the ACT key 110. The LCD 28 of the external infusion device 10 will show the word "SQUARE" and/or the dashes for the bolus amount will now blink (and/or an audible and/or vibration indication is provided). The user can press the Up arrow key (▲) 108 or the Down arrow key (▼) 112 to choose the desired square wave bolus portion amount. When the ACT key 110 is pressed, while a desired square wave bolus portion amount is displayed on the LCD 28, the square wave bolus portion duration will be then displayed (and/or an audible and/or vibration indication is provided). The user can then select the desired square wave bolus portion duration from 30 minutes to 8 hours (although other increments or duration's may be used). After the ACT key 110 is pressed for the desired square wave bolus portion duration, the external infusion device 10 will start delivering the normal bolus portion first. The square wave bolus portion will then start right after the end of the normal bolus portion. The word "BOLUS" and the amount of the bolus that has been delivered so fir will be displayed on the LCD 28 (and/or an audible and/or vibration indication will be provided). When the dual bolus is finished, the external infusion device 10 will beep (and/or vibrate) and display the amount of the bolus delivered for 5 seconds, then return to the normal time display. Alternatively, the external infusion device 10 may provide an audible indication by speech. In further alternative embodiments, the RF programmer 12' will have a display 150 and will provide visual confirmation of the square wave bolus, with or without an audio confirmation.

Other programming, commands, or data transfer may be accomplished by the RF programmer 12 (or remote commander), and the RF programmer 12 (or remote commander) should not be limited to the above-described Examples I–V. For instance, the RF programmer 12', since it includes a display 150 may use the same programming protocol and key sequences as those used to program the external infusion device 10 using the keypad 24 and LCD 28 on the external infusion device 10. Alternatively, the RF programmer 12' may use more sophisticated programming techniques, such as single key programming, if the display 150 includes the capability to use touch screen techniques, or may use additional keys in the keypad 152 that are specifically identified with particular programming features on the external infusion device 10.

Bolus Estimator

The Bolus estimator 14 (or carbohydrate estimator that estimates a bolus based on carbohydrate consumption (CHO)) assists the user with carbohydrate counting and in determining precise dosing adjustments to account for meals. Carbohydrates are the primary, but not the only, factor affecting blood glucose levels. Generally, it is sufficient to account just for the carbohydrates. It also encourages the user to enter current blood glucose values before using this feature, which will also be viewed quite favorably by the health care professional, since it increases compliance with the medical regimen and improves control. In alternative embodiments, the bolus estimator 14 in the external infusion device 10 can be connected or coupled to a glucose monitor by way of the RF programmer 12 (or other data transfer) to provide direct input to the bolus estimator 14.

In preferred embodiments, as shown in FIGS. 1, 6, 7 and 8(b), the bolus estimator 14 is used to assist the external infusion device 10 user with the estimations that are clone to determine the proper bolus amount that is needed to cover the anticipated carbohydrate intake at meals. The bolus estimator 14 does this by suggesting a bolus based on a pre-programmed carbohydrate ratio that is stored in the memory 22 of the external infusion device 10. The bolus estimator 14 will also take into account the user's insulin sensitivity and the differential between the user's pre-programmed target blood glucose (BG) level and the user's current BG level at the time the carbohydrate estimator 14 is activated. The recommendation, or result of the bolus estimator 14, is sometimes referred to as a "correction bolus".

Figure 8A:
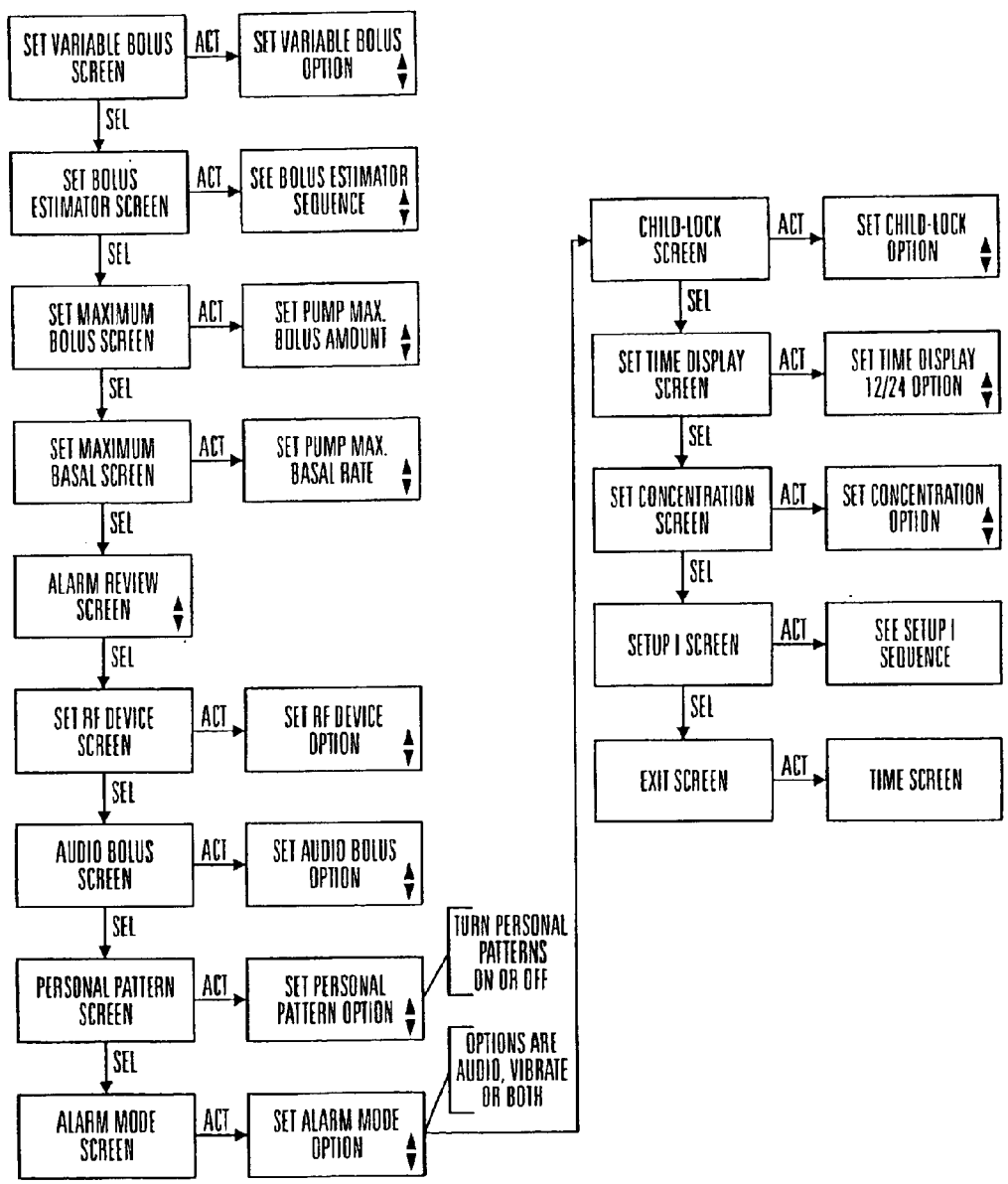
FIGS. 8(a) and 8(b) are flow diagrams illustrating the steps used to access the features of the setup II menu options shown in FIG. 6.
Figures 8B, 9:
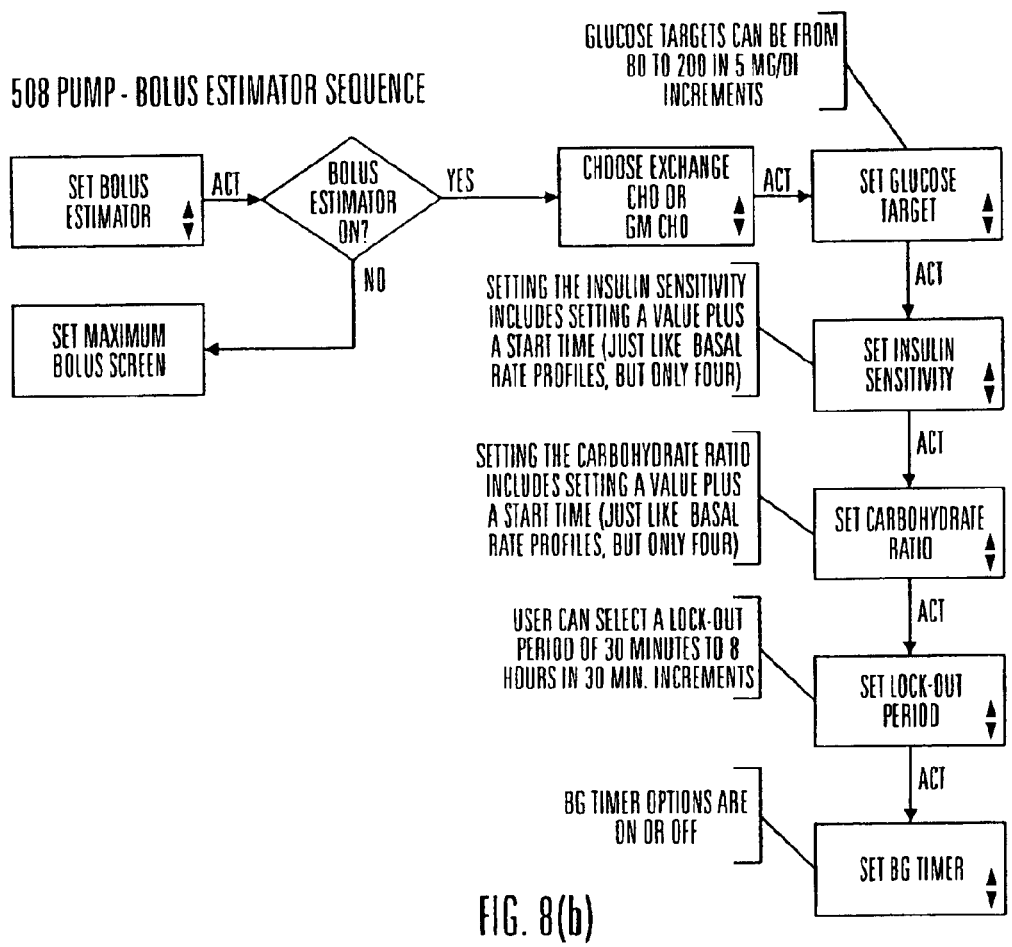
FIG. 9 is a table of the main menu options used on external infusion devices in accordance with embodiments of the present invention.
Figures 10, 11:
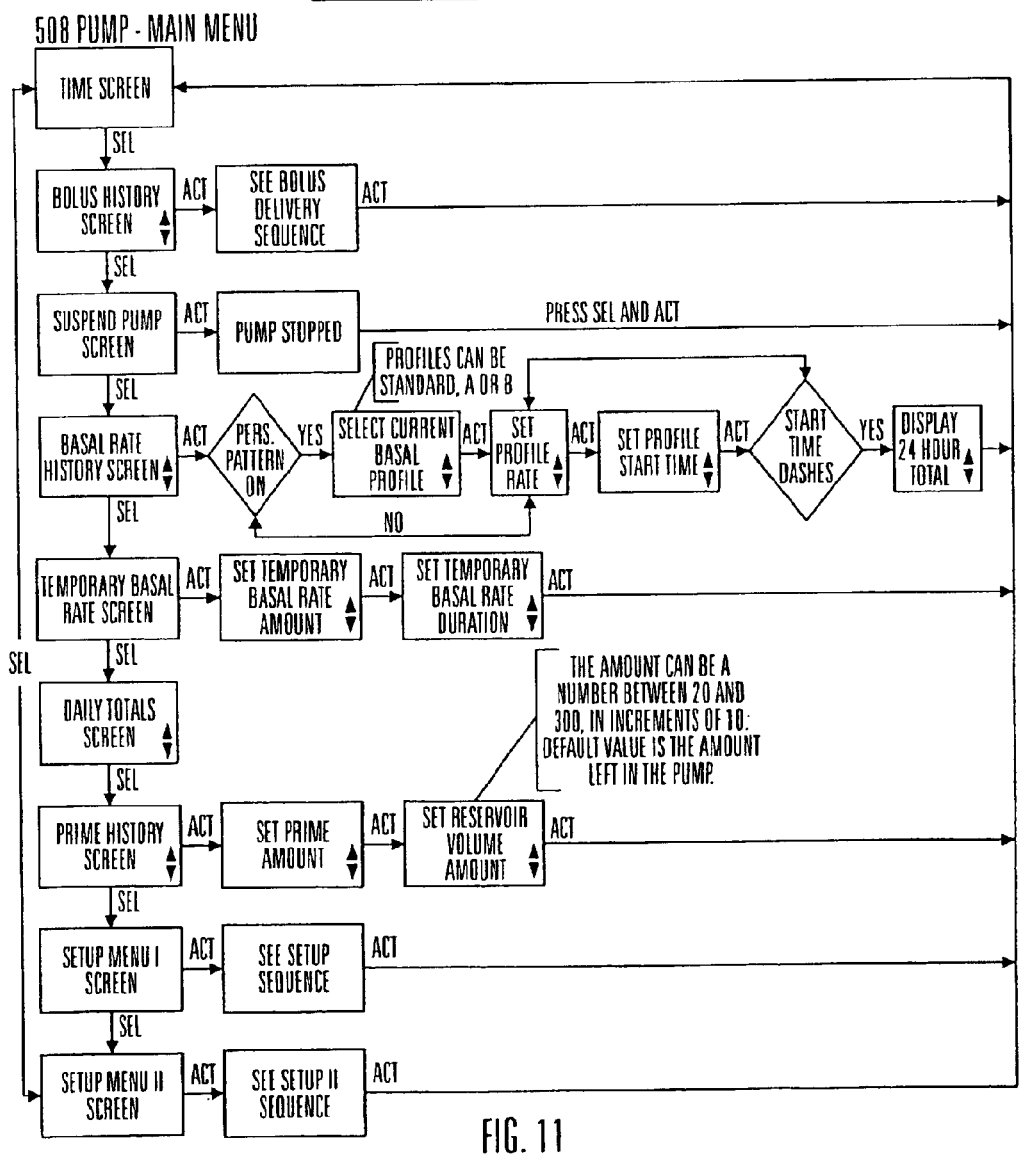
FIG. 10 is a table of Setup I menu options used on external infusion devices in accordance with embodiments of the present invention.
FIG. 11 is a flow diagram illustrating the steps used to access the main menu options shown in FIG. 9.
Figure 12:
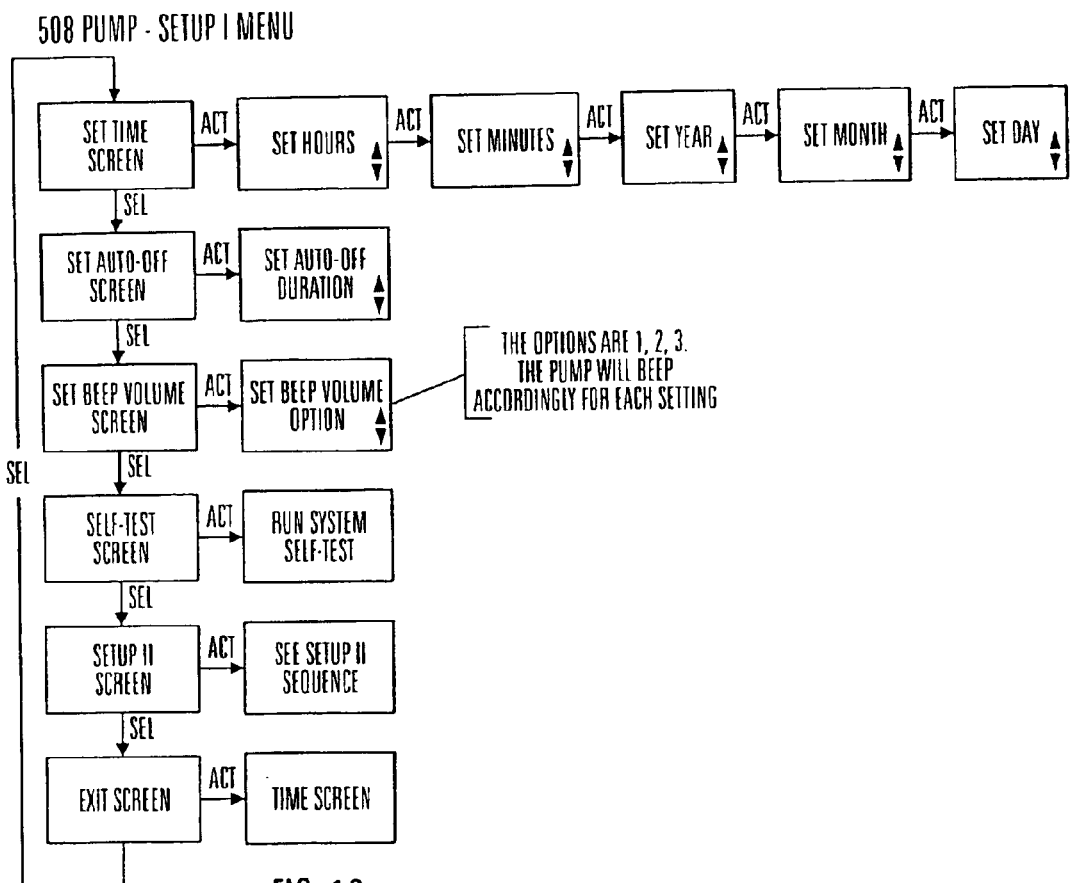
FIG. 12 is a flow diagram illustrating the steps used to access the features of the setup I menu options shown in FIG. 10.

The bolus estimator 14 is generally activated by the user, or preferably the health care professional, in the Set-up II menu of the external infusion device 10 (see FIGS. 6 and 8(b)), before it is operational, and preferably after the user has demonstrated a sufficient understanding of estimating carbohydrate intake. In preferred embodiments, the bolus estimator 14 is activated and programmed by using the keypad 24 on the external infusion device 10. However, in alternative embodiments, the bolus estimator 14 may be programmed and activated with an RF programmer 12 or 12'. In further alternative embodiments, the current glucose readings for the user my be provided by receipt of the glucose level measurement from a glucose monitor or via the RF programmer 12 to facilitate a correction for changing blood glucose (BG) levels. Further description of correcting infusion rates based on blood glucose readings may be found in U.S. Pat. No. 5,569,186 to Lord et al., entitled "CLOSED LOOP INFUSION PUMP SYSTEM WITH REMOVABLE GLUCOSE SENSOR," and U.S. Pat. No. 5,665,065 to Colman et al., entitled "MEDICATION INFUSION DEVICE WITH BLOOD GLUCOSE DATA INPUT", which are herein incorporated by reference. In alternative embodiments, the user may be able to use other combinations of the values to suggest different bolus types and amounts. In alternative embodiments, the carbohydrate estimator 14 can be used in a closed-loop system to augment the readings or check the closed-loop system's capability based on carbohydrate estimated meals. In still further embodiments, the bolus estimator 14 may be used to calculate correction boluses based on other parameters, with the type of bolus corrections being determined by the fluid being infused, body characteristics, or the like. Preferably, the bolus estimator 14 uses stored values or parameters related to the individual with current values, parameters or measurements and an algorithm to provide a recommended bolus that can be accepted, modified or rejected by the user. For instance in pregnancy, tocolysis may be infused and the measurement of the contraction rate may be used to suggest additional boluses of tocolysis medication. In HIV cases, a bolus amount of medication being infused may be adjusted based on a relationship to the current viral loads in the patient. In stroke or cardiac cases, the coagulation rate may be used to determine the bolus amount of heparin to be administered. Other calculations may be made and should not be limited to the above-described examples.

After the bolus estimator 14 has been enabled, the user will be prompted to store the following three (3) values in the memory 22 of the external infusion device 10. In alternative embodiments, more or fewer values may be needed or used. These values are used by the bolus estimator 14 and the processor 18 of the external infusion device 10 to perform the necessary calculations in suggesting a bolus amount. In preferred embodiments, access to programming and changing these values may be restricted to the health care professional. In alternative embodiments, these values can be restricted to entry through an RF programmer 12 or a connection of the external infusion device 10 with a programming device, such as a PC, laptop or the like. The inputted values needed to be stored for the bolus estimator 14 are:

Target Blood Glucose (Target), which is the target blood glucose (BG) that the user would like to achieve and maintain. Generally, the programmable blood glucose (BG) values for this range are between 60 to 200 in five unit increments. Preferably, the carbohydrate calculator has the capability to accept values that range between 20 to 600 in 1 unit increments to cover a large number of possible scenarios. However, in alternative embodiments, different ranges and increments may be used.

Insulin Sensitivity (Set Sens), which is a value that reflects how far the user's blood glucose drops in milligrams per deciliter (mg/dl) when one unit of insulin is taken. Preferably, the programmable values for this range are between 5 to 180 in one unit increments. However, in alternative embodiments, different ranges and increments may be used. In preferred embodiments, insulin sensitivity is programmable for up to four different time periods, the use of which will require four separate profiles to be stored in the memory 22. Setting the Insulin Sensitivity profiles is similar to setting the basal profiles. In alternative embodiments, more or fewer time periods (and corresponding profiles) may be used.

Carbohydrate Ratio (Set Carbs), which is a value that reflects the amount of carbohydrates that are covered by one unit of insulin. Generally, the values are in the range of 1 to 300 in increments of 1 unit (or, alternatively, in ranges of 0.1 to 5.0 in increments of 0.1 for carbohydrate exchanges). Preferably, the programmable values for this range are between 5 to 30 in one unit increments. However, in alternative embodiments, different ranges and increments may be used.

As a safety precaution, the user or healthcare professional may also set a Lockout Period, which takes into account the pharmacokinetic effect of insulin when suggesting a bolus. The purpose is to prevent a successive use of a correction bolus when the pharmacokinetic effects of the previous bolus have not yet been accounted for. The programmable values for this range are between 30 minutes to 240 minutes, programmable in 15 or 30 minute increments. However, in alternative embodiments, different ranges and increments may be used. In further alternative embodiments, the lock out period may be automatically calculated based on boluses recently delivered and/or canceled based on new blood glucose (BG) readings. In other embodiments, the carbohydrate calculator 14 may include a programmable reminder to check the post-prandial blood glucose value to determine if additional boluses and or corrections should be made at a later time after the meal. The programmable reminder values are between 30 minutes to 240 minutes, programmable in 15 or 30 minute increments. However, in alternative embodiments, different values and increments may be used.

After the above values are set in the memory 22 of the external infusion device 10, the bolus estimator 14 will suggest a bolus based on the entry of the estimated carbohydrate intake and current and target blood glucose (BG) levels. The calculation will only be performed if the three values are programmed and stored in the memory 22. Preferred embodiments use the following equation:

$$Bolus = \frac{(CurrentBG - TargetBG)}{InsulinSensitivity} + \frac{CarbohydratesToBeConsumed}{CarbohydrateRatio}$$

If the user wishes the external infusion device 10 to suggest a bolus for the estimated carbohydrate intake only, then the only value they need to program is for the Carbohydrate Ratio, and the BG portion of the equation will be ignored. In alternative embodiments, variations or different equations may be used.

In operation, once the bolus estimator 14 has been enabled and the above listed values have been programmed into the memory 22 of the external infusion device 10, the bolus estimator 14 can be used to suggest a correction or meal bolus. The user may then accept or change the bolus amount suggested by the bolus estimator 14. In one embodiment, processor 18 stores in memory 22 a record of whether the suggested bolus amount from the bolus estimator 14 was accepted or changed by the user, and records the suggested and changed bolus amounts. The stored data can be used for later analysis by downloading the data to a computer by RF or IR transmissions, for example by IR transmissions from the external infusion device 10 through the communication station 8 to the computer 6, as shown in FIG. 15, or the like. The following examples illustrate hypothetical carbohydrate calculation scenarios. The examples show use of the bolus estimator 14 by the keypad 24 on the external infusion device 10. However, it should be understood that the bolus estimator 14 could be activated and programmed by the RF programmer 12 or the like. Alternatively, the keypad 24 (or RF programmer 12) may include an additional key.

Preferred embodiments use a normal bolus. In alternative embodiments, the user may be given the choice of a normal, dual, square wave bolus, extended bolus, profiled bolus, or the like, by enabling these capabilities on the variable bolus menu in the Setup II menu (see FIGS. 6 and 8) on the external infusion device 10. If the variable bolus capability is not enabled, then every bolus would be a normal bolus. As discussed, preferred embodiments of the present invention use normal one time boluses. However, alternative embodiments may utilize different bolus types to spread out the correction or meal bolus determined by the carbohydrate estimator 14.

The same set of pre-programmed values as described above and shown below in Table 1 will be used for each of the following examples VI–IX:

Table 1

Pre-programmed Values for the Examples

| Pre-programmed Values | |
|---|---|
| Target BG: | 100 |
| Insulin Sensitivity: | 30 |
| Carbohydrate Ratio: | 15 |
| Lockout Period: | 60 |

EXAMPLE VI

Bolus Estimator—Square Wave

The user presses the SEL key 114 and then the ACT key 110 on the external infusion device 10 to choose a "Normal" bolus, and uses the ACT key 110 to select the carbohydrate estimator 14. To operate the bolus estimator 14, and assuming that the user measures his/her blood sugar level to be 160 mg/dl, and assuming the user estimates that a meal of 75 grams of carbohydrates is to be consumed, the following "dialog" occurs between the user and the external infusion device 10:

External infusion device 10 Prompt: "Enter BG" (preferably, there will be three dashes in the upper right corner of the display—although other displays or indications may be used).

User: Enters the value "160" by scrolling the Up arrow key 10 and pressing the ACT key 110. 160 is displayed and then entered.

External infusion device 10 Prompt: "# gm CHO" meaning the number of grams of carbohydrate to be consumed (there will be three dashes in the upper right corner of the display—although other displays or indications may be used).

User: Enters the value "75" by scrolling the Up arrow key (▲) 108 and pressing the ACT key 110. 75 is displayed and then entered.

External infusion device 10 Prompt: Suggests a "7.0" unit bolus (2 units of correction and 5 units to account for the carbohydrates to be consumed).

User: Can accept the suggested bolus by pushing the ACT key 110 or use the Up arrow key (▲) 108 or the Down arrow key (▼) 112 to select a different bolus amount, and then presses the ACT key 110 to start the bolus.

EXAMPLE VII

Bolus Estimator—Dual Wave

The user presses the SEL key 114 and chooses a "Dual" wave bolus, and then the ACT key 110. To operate the bolus estimator 14, and assuming that the user measures his/her blood sugar level to be 160 mg/dl, and assuming the user estimates that a meal of 75 grams of carbohydrates is to be consumed, the following "dialog" occurs between the user and the external infusion device 10. The following "dialog" will then take place between the user and the external infusion device 10:

External infusion device 10 Prompt: "Enter BG" (there will be three dashes in the upper right corner of the display—although other displays or indications may be used).

User: Enters the value "160" by scrolling the Up arrow key (▲) 108 and pressing the ACT key 110. 160 is displayed and then entered.

External infusion device 10 Prompt: "# gm Carbs" which means the number of grams of carbohydrate to be consumed (there will be three dashes in the upper right corner of the display—although other displays or indications may be used).

User: Enters the value "75" by scrolling the Up arrow key (▲) 108 and presses the ACT key 110. 75 is displayed and then entered.

External infusion device 10 Prompt: Suggests a "7.0" unit bolus.

User: Can accept the suggested bolus by pressing the ACT key 110 or use the Up arrow key (▲) 108 or the Down arrow key (▼) 112 to select a different bolus amount.

External infusion device 10 Prompt: "Now" with the accepted value of "7.0" units blinking. Typically the user will scroll down using the Down arrow key (▼) 112 to select only part of the bolus now. Lets say the user selects "2.0" and presses the ACT Key 110.

External infusion device 10 Prompt: "Square" will appear on the screen with the remainder of the bolus (i.e., "5.0") blinking. The user can again select this amount or scroll to a different amount. The duration will be set by activating the SEL key 114 and incrementing the time.

EXAMPLE VIII

Bolus Estimator—Square Wave—Lower BG

The user presses the SEL key 114 and then the ACT key 110 on the external infusion device 10 to choose a "Normal" bolus, and uses the ACT key 110 to select the bolus estimator 14. To operate the bolus estimator 14, and assuming that the user measures his/her blood sugar level to be 70 mg/dl, and assuming the user estimates that a meal of 75 grams of carbohydrates is to be consumed, the following "dialog" occurs between the user and the external infusion device 10:

External infusion device 10 Prompt: "Enter BG" (there will be three dashes in the upper right corner of the display—although other displays or indications may be used).

User: Enters the value "70" by scrolling the Up arrow key (▲) 108 and pressing the ACT key 110. 70 is displayed and then entered.

External infusion device 10 Prompt: "# gm Carbs" which means the number of grams of carbohydrate to be consumed (there will be three dashes in the upper right corner of the display—although other displays or indications may be used).

User: Enters the value "75" by scrolling the Up arrow key (▲) 108 and presses the ACT key 110. 75 is displayed and then entered.

External infusion device 10 Prompt: Suggests a "4.0" unit bolus (−1 unit correction and 5 units to account for the carbohydrates to be consumed).

User: Can accept the suggested bolus by pressing the ACT key 110 or use the Up arrow key (▲) 108 or the Down arrow key (▼) 112 to select a different bolus amount.

Preferred embodiments of the bolus estimator 14 utilize general miles to minimize the potential for inaccurate results from the bolus estimator 14 or administering a bolus at an inappropriate time. For instance, if a correction bolus has been previously given such that the BG Now>BG Target, then the Lockout period is activated and the bolus estimator 14 will not calculate a correction bolus. In alternative embodiments, the bolus estimator 14 may determine a bolus based on carbohydrates to be consumed and omit the portion of the calculation that utilizes the blood glucose level to determine the correction portion of the bolus. Thus, the external infusion device 10 will not prompt the user with "Enter BG" during the Lockout period, and will effectively operate only as a carbohydrate estimator. Once the Lockout period has expired, the external infusion device 10 will prompt the user for a current BG value, and then suggest a correction bolus if the user enters a current BG value. Also, if the bolus estimator 14 estimates a bolus to be a negative value (BG is below target and carbohydrate intake amount is minimal) then the external infusion device 10 will display "No Bolus!" as a warning. Also, if the user enters a current blood glucose (BG) level that is lower than a certain value, such as 50 (although other values may be used), the external infusion device will display "Low BG".

EXAMPLE IX

Bolus Estimator—Insulin Duration Factor

A further embodiment of the bolus estimator 14 may include the ability to account for the effects of recently taken insulin that is still, at least partially, still active in the body of the user. The concern would be that the remaining insulin could have the effect of lowering the blood glucose level too quickly, or too far, if the remaining insulin was not accounted for. Thus, this embodiment utilizes an Insulin Duration Factor to account for the effects of the insulin still remaining in the body.

The Insulin Duration Factor would also be a programmable parameter that is in the Setup II section of the pump along with the other parameters, as described above. The user would program the approximate duration time that insulin is active in their system. For instance, users of fast acting insulin analogs would program 1 to 4 hours in 15 or 30 minute intervals, and users of Regular insulin would program 2 to 8 hours in 15 or 30 minute intervals. However, in alternative embodiments, different values and increments may be used. Preferably, the insulin duration factor should be selected and adjusted by the health care professional or the user upon recommendation and/or consultation with the health care professional. Preferred embodiments use the following equation (note if a negative value is returned (i.e., the insulin from a previous bolus is used up) the equation will return a value of 0 for no insulin remaining to avoid over correcting):

$$InsulinRemaining = \frac{(InsulinDurantionFactor - TimeSinceLastBolus)}{InsulinDurationFactor} \quad \text{If} \geq 0$$

Otherwise

Insulin Remaining = 0

In this example, it is assumed that the user programs a 3 unit correction bolus at 11:00 am to correct for a 190 BG value. The user then decides to use the bolus estimator 14 at 12 Noon to estimate a bolus for meal containing 75 grams of carbohydrate. The Insulin Duration Factor is set to 3 hours.

The user presses the SEL key 114 and then the ACT key 110 on the external infusion device 10 to choose a "Normal" bolus, and uses the ACT key 110 to select the bolus estimator 14. To operate the bolus estimator 14, and assuming that the user measures his/her blood sugar level to be 160 mg/dl, and assuming the user estimates that a meal of 75 grams of carbohydrates is to be consumed, the following "dialog" occurs between the user and the external infusion device 10:

External infusion device 10 Prompt: "Enter BG" (preferably, there will be three dashes in the upper right corner of the display—although other displays or indications may be used).

User: Enters the value "160" by scrolling the Up arrow key 10 and pressing the ACT key 110. 160 is displayed and then entered.

External infusion device 10 Prompt: "# gm CHO" meaning the number of grams of carbohydrate to be consumed (there will be three dashes in the upper right corner of the display—although other displays or indications may be used).

User: Enters the value "75" by scrolling the Up arrow key (▲) 108 and pressing the ACT key 110. 75 is displayed and then entered.

Insulin Remaining: 3.0 (Insulin Taken)×⅔(Insulin Duration Remaining)=(2.0) units.

External infusion device 10 Prompt: Suggests a "5.0" unit bolus (2 units of correction and 5 units to account for the carbohydrates to be consumed and a subtraction to account for the remaining insulin in the user).

User: Can accept the suggested bolus by pushing the ACT key 110 or use the Up arrow key (▲) 108 or the Down arrow key (▼) 112 to select a different bolus amount, and then presses the ACT key 110 to start the bolus.

Since the external infusion device 10 stores the time of each bolus delivery, the above simple algorithm can be designed to take into account the amount of insulin that might still be remaining in the user's body from a previous bolus. The longer the programmed time for the "Insulin Duration Factor" then the more conservative the estimate becomes. In further embodiments, the external infusion device 10 could adjust for several boluses that were delivered within the insulin duration window. Although it is difficult to predict how long insulin will actually remain active in the body, the above described algorithm does at least consider the effects on the amount of insulin actually needed. This provides an additional level of conservative estimation in the external infusion device 10 by accounting for insulin delivered within a programmable window. Without such an algorithm, in the example above the pump would have suggested a "7.0" unit bolus because the remaining insulin would not have been accounted for in the suggested bolus.

The bolus estimator 14 has the advantage of prompting the user to enter his/her blood glucose (BG) value, and thus serves as a useful reminder to check BG levels regularly. This makes testing more advantageous then ever, since the results directly assist the user in maintaining control of his/her condition. Also, the bolus estimator 14 enables the external infusion device 10 to capture information on carbohydrate intake which is valuable for helping the user to refine carbohydrate counting skills. This data may also be downloaded to a PC, laptop, Communication-Station, RF programmer, or the like.

In further embodiments, an external infusion device 10 and user can utilize the bolus estimator 14 information to "learn" insulin sensitivity values, carbohydrate counting, the effects of high fat meals and other variables that can lead to better control, and use this to adjust the results of the bolus estimator 14. In alternative embodiments, the user can omit entering specific carbohydrate amounts each time calculations are made by the user. For instance, the external infusion device 10 may store the carbohydrate amounts for several meals that are regularly eaten by the user in the memory 22, and then allow the user to recall the stored meals. In other alternative embodiments, a list of general foods may be provided with a carbohydrate equivalent. In still further embodiments, the external infusion device 10 may utilize a more complicated keypad and/or RF programmer 12, and a code is assigned for each food. Then the code for each food to be consumed is entered into the external infusion device 10.

Vibration Alarm

Further embodiments of the present invention include a vibration alarm 16 that provides a noticeable vibration in addition to or in lieu of an audible alarm. The resulting tactile sensation of the vibration make the alarms more noticeable during sleep, when not thinking clearly due to various conditions, or the like, to improve the likelihood that the user will respond to an alarm. Thus, a vibration alarm 16 can improve safety and control. In addition, the vibration alarm 16 may be less publicly noticeable, and thus more useable in quiet settings, such as libraries, lectures, shows, or the like, or in loud settings where the alarm might go unnoticed, such as parties, concerts, or the like. In further embodiments, the RF programmer 12 may include a vibration alarm (not shown) that can deliver a vibration alarm to the user in addition to, or instead of, the vibration alarm 16 from the external infusion device 10. Alternatively, the RF programmer 12 may provide a vibration alarm and the external infusion device 10 may provide an audible alarm or vice versa.

The vibration alarm 16 also provides an additional capability used during priming or operation of the external infusion device 10. It has been found that activating the vibration alarm 16, before or during priming, will assist in removing air bubbles in the reservoir or tubing. This procedure minimizes the amount of medication that must be expelled to clear the air bubbles, by allowing bubbles to move towards the outlet and the tubing based on the agitation of the reservoir. Use of the vibration alarm 16 during priming can result in substantial savings when using expensive or concentrated medications with the external infusion device 10. This also simplifies and somewhat automates the priming of the external infusion device 10. In addition, the vibration alarm 16 may be used to agitate the medication (such as suspensions of a drug) during administration so as to minimize sedimentation or separation of the medication, or, if power requirements are an issue, between infusion increments of the fluid by the external infusion device 10, if such agitation is desired.

Other Capabilities

Particular embodiments will include a "Low Reservoir Alert". The alert will sound when the plunger of the external infusion device 10 reaches the point where approximately 0.200 ml of fluid remains in the reservoir. However, in alternative embodiments, larger or smaller activation thresholds may be used. An icon indicating "Low Volume" will appear on the main LCD 28 screen until the condition is corrected. If correction of the low volume has not happened at an approximate level of 0.100 ml, the external infusion device 10 will beep again. However, in alternative embodiments, larger or smaller activation thresholds may be used. Preferably, the external infusion device 10 will keep track of the reservoir volume in the software and request the user to update the reservoir volume manually whenever the prime function is activated.

Other embodiments may utilize a "Take a Break Bolus". This is particularly well adapted for short acting medications or fluids. The purpose of this capability is to deliver an extra bolus before disconnecting from the external infusion device 10, to make certain that the clinically needed amount of medication or fluid is delivered before interrupting the administration. This will help the user remain above the minimum therapeutic level during an interruption of medication or fluid delivery. Preferably, four durations of an interruption of the medication or fluid infusion will be possible: 30 minutes; 1 hour; 1 hour and 30 minutes; and 2 hours. However, additional, or longer or shorter intervals may be used. Generally, this capability is activated in the Setup II menu by the health care specialist, who will program the dose for each of the 4 possible times of delivery interruptions. The dose is set based on the medication or fluid and the condition of the user. If the health care specialist programs only certain durations (for example 30 minutes and 1 hour only), the user will only be able to take a break for those durations. In preferred embodiments, in the "Take a Break Bolus" screen, the user will program the duration of the planned interruption. The external infusion device 10 will then beep after the delivery of the previously set dose. The user will then disconnect from the external infusion device 10 and will be reminded by the external infusion device 10 to reconnect when the time is up. Preferably, the reminder alarm will continue to sound (or vibrate) until the user reactivates the external infusion device 10.

Particular embodiments include a "Lockout function". Preferred embodiments will have multiple lockout levels, with the selection be dependent on the anticipated usage, the external infusion device model, the sophistication of the user, or the like. For instance, the following lockout levels may be used (a lockout levels means that some of the features of the external infusion device will not be accessible to the patient (or user), but will be accessible to the Health Care Professional or the parent of a child using the external infusion device 10):

"None" (0) will let the user program and access all features of the external infusion device 10;

"Setup" (1) will lock the user out of changing both Setup I and Setup II parameters. The user will only have access to activated features of the external infusion device 10, but can not change the pre-set parameters. The user will be able to review the settings, and only change the lockout level with an authorized key sequence. The only Setup feature that will still be available is Selftest.

"All except Suspend" (2) will only allow the user to suspend the external infusion device and to perform a Selftest. All other features will be locked out. The user will be able to review the settings, and only change the lockout level with tan authorized key sequence.

The "Lockout function" will be in Setup II. A special key sequence (or code) will be required to change the lockout level. This will minimize the possibility of an unauthorized change of the lockout levels. In preferred embodiments, an icon (lock) will be displayed on the LCD 28 when the external infusion device 10 is in Lockout mode 1 or in Lockout mode 2.

Preferred embodiments of the external infusion device 10 will include a configurable menu that is accessible by password through the use of a PC, laptop, RF programmer or the like. This ability allows the physician, or sophisticated user, to select only the external infusion device 10 capabilities that are required for an individual user. A "lock out" capability will enable the physician to exclude certain options from the user. This may be useful with new users or children using the external infusion device 10.

Further embodiments may include a "Suspend/Storage Mode". In addition to the regular Suspend Mode (discussed above), the external infusion device 10 can be put in a "Storage Mode" in which no recurring alert (beeping and/or vibrating) will remind the user of the external infusion device 10 being in the "Storage Mode". Thus, for example, in "Suspend Mode", the external infusion device 10 will display the time of day, STOPPED and -S- on the LCD 28. In addition, the external infusion device 10 will beep (and/or vibrate) 6 times every 30 minutes as a reminder. In suspend "Storage Mode", the external infusion device 10 LCD 28 will display the -S- only and will not repeatedly beep (and/or vibrate).

In preferred embodiments, software options will appear as choices for the user if they are first selected from the Main Menu, the Setup I and Setup II screen, as shown in FIGS. 6–12. The physician will also be able to control what range of choices are available for the user, either in the office or remotely through a PC connected to a Communication-Station. In preferred embodiments, the external infusion device 10 will have the ability to transmit all the stored memory content to a Computer 6 or external FAX/Modem connected to a Communication-Station 8, as shown in FIG. 15. Further description of a Communication Station of this general type is be found in U.S. Pat. No. 5,376,070 to Purvis et al., entitled DATA TRANSFER SYSTEM FOR AN INFUSION PUMP, which is herein incorporated by reference.

Preferred embodiments, use scrollable menus to set various capabilities. In alternative embodiments, different menu structures or ways of moving through the menus may be used. In preferred embodiments, the user presses the SEL key 114 to scroll the external infusion device 10 through a series of informative displays or Select States (e.g., main menu, setup I and setup II—see FIGS. 6–12). The displays differ depending upon the current status (state of software execution) of the external infusion device 10.

Preferably, the programming capabilities that are accessed infrequently are kept in the Setup menus. The external infusion device 10 has two layers of setup menus, Setup I and Setup II. Setup I contains capabilities that are used more often than those in Setup II. Both Setup I and Setup II menus will be accessible through the main menu by pressing the SEL key 114 at the links between the Setup I and Setup II (see FIGS. 6–12). The Setup I menu (see FIGS. 10 and 12) will be entered by pressing the ACT key 110, while the Setup I screen is being displayed. While in the Setup I menu, the screens that are displayed are Time Adjustment, Automatic Off Duration, Beep Volume, User Self Test, Setup II and Setup Exit. The Setup II menu (see FIGS. 9 and 11) can be entered by pressing the ACT key 110 while the Setup II screen is being displayed. While in the Setup II menu, the screens that are displayed are Audio Enhanced Bolus Mode On/Off & Increment, Variable Boluses Mode On/Off, Bolus Estimator (carbohydrate calculator), Maximum Bolus, Maximum Basal rate, Time Mode (12/24 hour display), Insulin Concentration, Alarm Review, Alarm Mode, Childlock (lock-out), Set RF Device, Personal Delivery Patterns, Setup I and Setup Exit.

Generally, none of the values can be changed directly from the Select States. To alter a value on an informative display, the user must first press the ACT key 110. This is referred to as entering a Set State. The word "SET" will appear on the display (and/or an audible and/or vibration indication is provided), and the value that can be changed will be blinking. Pressing the Up arrow key (▲) 108 or the Down arrow key (▼) 112 will change the blinking value. After scrolling to the desired value, the ACT key 110 must be pressed again. This will activate the new value and return the external infusion device 10 to the normal operating (time) display. If more than one value can be changed on a single display, pressing the ACT key 110 will cause the other value to be selected and the Up arrow key (▲) 108 and the Down arrow key (▼) 112 will affect this next value. Two general exceptions to the preferred rule governing the parameter selection described above are the normal operating (time) display and the Total History state. Both are Select States. When the normal operating (time) display is in effect, pressing the ACT key 110 will show the user the amount of battery power left, or, alternatively, or in addition to, the amount of medication remaining in the reservoir (thus time cannot be changed from it, since time setting is handled in the SetUp I menu). The Total History state is for information only. Historical total values may be viewed directly from the select state with the arrow keys.

In preferred embodiments, if the external infusion device 10 is left idle while in a Set State, the software will return to the time display state after approximately 15 seconds, no changed values will be activated. If the external infusion device 10 is left idle in a Select State, it will return to the time display state in approximately 7 seconds. In alternative embodiments, longer or shorter time periods for the various states may be used.

The external infusion device 10 will preferably include the following. Select States in the main menu (see FIGS. 9 and 11): time display, bolus history, suspend, basal rate, temporary basal rate, total history, prime bolus, Setup I menu and Setup II menu. The Setup I menu (see FIGS. 10 and 12) will feature the additional select states: time and date adjustment, automatic off duration, beep volume, user self test, Setup II, and Setup exit. The Setup II menu (see FIGS. 6 and 8) will feature the following options: audio enhanced bolus mode enable/disable & increment, variable bolus mode enable/disable, maximum bolus, maximum basal rate, bolus estimator setting, personal delivery pattern selection, alarm clock setting, insulin concentration, alarm review, lock-out, RF programmer set up, Setup I, and Setup exit. After a capability is activated in any Set State in the normal operating menu, the normal operating display (time display) will be displayed. In alternative embodiments, other values may be displayed.

Preferably, after a capability is activated in one of the Setup menus, the next Setup Select State will be displayed. Once in one of the Setup Menus, the user may use the SEL key 114 to view all of the Setup Select States until the keyboard is allowed to time out (in approximately 15 seconds) or the user presses the ACT key 110 on the Exit Setup state.

Preferably, the SEL key 114 is used to select an option. For safety, using this key will never change any value. If there is more than one option in a single programming sequence (Set State), such as hours, minutes, and date on the time setting display, the options are selected with the ACT key 110. The ACT key 110 is used to allow changing of values by entering set states, and to activate changed values. The Up arrow key (▲) 108 and the Down arrow key (▼) 112 are available as valid keys when numbers or dashes are blinking. However, in preferred embodiments, there are two exceptions: while normal operating (time) screen is displayed, 1) pressing the Up arrow key (▲) 108 invokes the audio enhanced bolus function if enabled in setup II; and 2) pressing the Down arrow key (▼) 112 turns on the LCD backlighting. The backlight will remain on for about fifteen seconds after the last key press. Any key press before the expiration of fifteen seconds will restart the fifteen second time-out.

The external infusion device 10 can be programmed to deliver up to forty-eight basal rates daily. The user does not need to program all forty-eight rates. The multiple basal rates are called profile segments. Profile segments are preferably programmed with a start time and a basal rate. A profile segment rate will become active at the profile segment start time. This allows for several different delivery schedules to occur without requiring the user to reprogram the external infusion device 10. The first profile segment always begins at midnight. The other profile segments always start on even hour or half-hour boundaries. The delivery pattern will repeat daily. In alternative embodiments, the external infusion device 10 may contain more, or less, than forty eight profiles, with amount being dependent on memory, time increment for each profile, and the like.

A Setup option will allow the user access to three "personal patterns" in order to accommodate individual lifestyle requirements. The first personal pattern is the current basal profile pattern. The second personal pattern will follow the first personal pattern and a "2" icon will be displayed by the external infusion device at all times, on the main screen and the basal screen. The third pattern will follow the second pattern and display a "3"icon at all times. The patterns will be presented to the user in a circular manner until the user selects dashes as the time for the next basal rate. The user will choose their personal pattern by selecting a 1, 2, or 3 in the setup II menu. The user will know which pattern is current by looking for either a blank (i.e., pattern 1 is on), a "2" icon (i.e., pattern 2 is on), or a "3" icon (i.e., pattern 3 is on).

Preferably, the user, or healthcare professional, may program two separate limits into the external infusion device 10. A maximum meal bolus can be set to limit the size of meal boluses. When setting a meal bolus the software will not allow the scrolling to exceed the maximum. There is also a maximum basal rate that limits the rate of profile segments and the temporary basal rate. When setting profile segment rates or a temporary basal rate, the software will not allow any values greater than the maximum basal rate.

The meal bolus history function will allow the user to view the last twelve meal boluses in reverse-chronological order. The Up arrow key (▲) 108 and the Down arrow key (▼) 112 are valid from the Select State. The most recently delivered bolus will be displayed as bolus history 1. Older boluses will be histories 2 through 24. The display of the most recent bolus will show the word "LAST." The display of the older boluses will show the day of the week that they were delivered, for safety reasons, the historical meal boluses may not be changed.

The external infusion device 10 will maintain a history of the daily totals for the last 90 days. The user can only display the last 7 days through the pump's display, (generally 90 days are accessible by downloading only—although other numbers of days may be used). This display is accessed as a Select State. The day for the total may be scrolled to view total history directly from the display state. The total delivered Select State will have the day (displayed as "TODAY" for today's date or DayMonthYear [01SEP97] for any other day) blinking. When the day is scrolled, the display shows the corresponding day's total.

The user will be able to review the last 200 events that occurred to the pump. Generally, these may be reviewed on the LCD 28 of the external infusion device 10. Alternatively, the events are only available by downloading the data through the transmitter/receiver 26 (for example using IR serial communication) of the external infusion device 10. Typical types of events that can be received or downloaded are: time adjustment; auto-off duration; maximum bolus; maximum basal rate; insulin concentration; suspend on; suspend off; basal rate profile; temp. basal rate; battery removal and battery replacement, and carbohydrate estimator stored set values and history. The external infusion device 10 may be capable of communicating via its bi-directional telemetry. It will be capable of sending data and receiving and executing commands according to a well-defined protocol.

The LCD 28 of the external infusion device 10 introduces the capability to use icons for easier identification and use. For example, the following icons are available: a clock alarm icon, a low battery alarm icon, a low insulin alarm icon, and one or more personal pattern icons. In alternative embodiments, more or fewer icons may be used. The use of icons makes all understanding of the display and alarm conditions easier, thus increasing safety and efficient use of the external infusion device 10.

Alarms will be easily recognizable while providing the user with the information they need to make an informed decision. The alarms may be displayed on the LCD 28, provided audibly through the speaker 30 and/or using the vibration alarm 16. An alert will sound when the plunger reaches the point where approximately 20 units of insulin (U-100) remain. In alternative embodiments, more or fewer remaining units may be used, and/or the units remaining may be programmable by the user or healthcare professional. An icon indicating "Low Volume" will appear on the main screen, and/or other alarms may be provided, until the condition is corrected.

Preferred embodiments will include an alarm clock. The user will determine and set an amount of time, preferably from 30 minutes to 24 hours, although longer or shorter periods may be set. The external infusion device 10 unit will provide an alarm and will prompt the user to repeat the same alarm frequency or cancel the alarm. The alarm will assist in warning the user on when to test blood glucose levels, inject insulin or the like. Alternative embodiments may include multiple alarms and different tones to permit more precise control and monitoring.

In preferred embodiments, all alarms will gradually escalate in frequency or volume so that the user can terminate them as soon as they are noticed. In alternative embodiments, the alarms may change tones or intermittently stop to draw attention to the alarm condition. In further alternatives, the external infusion device 10 may use the transmitter/receiver 26 to transmit the alarm to a remotely located device, such as a Communication-Station, modem or the like to summon help.

In preferred embodiments, there is also a maximum number of external infusion device 10 strokes for the drive mechanism 32 that may occur in one hour based on the maximum basal rate and bolus amounts. The external infusion device 10 will sound (or vibrate) and the external infusion device 10 will not be able to deliver more than ((2.5*maximum bolus)+maximum basal+1) strokes in one hour. Preferably, the external infusion device 10 will deliver medication in 0.1 units volume increments (although other increments may be used). The actual amount of insulin or medication in a given stroke depends on the insulin or medication concentration, stroke length and delivery reservoir diameter or cross-sectional area. In preferred embodiments, the delivery rates are scrolled by the amount of insulin per stroke. The rate delivery pattern will be calculated by dividing the number of strokes required for the rate into 3600 (the number of seconds in one hour). The result is the number of seconds between each stroke. The rate will be delivered evenly over the hour, each stroke on a one-second boundary. Rates that do not divide evenly into 3600 will not have any accumulating error. For example, consider a rate of 3.0 units per hour and a concentration of U-100. 3.0 U/hr at U-100 will require 30 strokes per hour. This translates to a pump stroke every 3600/30=120 seconds, or one stroke every two minutes. In alternative embodiments, the drive mechanism 32 may provide for continuous flow rather than incremental or pulsed flow rates. Further alternatives may omit strokes and utilize hydraulics, pneumatics, step motors, continuous motors, or the like.

The external infusion device 10 will support drug delivery in U-400, U-250, U-200, U-100, U-50 and U-40 concentrations of insulin. In alternative embodiments, the external infusion device 10 will support drug delivery in insulin concentrations below U-40 and above U-400, such as U-500 and U-1000. The amount of insulin delivered per pump stroke depends upon the concentration. If the concentration is changed, the constant factors which convert pump strokes into units of insulin are changed accordingly. Preferably, when a new concentration is selected, all settings except the time of day and day of week return to the factory default settings. The default concentration is U-100. In alternative embodiments, different default concentrations may be set being dependent on the type of fluid to be infused, and different or no settings will return to the factory defaults. Preferred embodiments of the external infusion device 10 will utilize a conventional plastic (such as the MiniMed MMT-103) reservoir. Alternative embodiments may use reservoirs formed out of other materials, such as glass, metal or the like; and the reservoir may be pre-filled or filled by the user prior to use in the external infusion device 10.

Preferred embodiments of the external infusion device 10 can be dropped in water without causing damage to the pump. (IEC601-1 IPX7 watertight standard—although other levels of water resistance or standards may be used). The external infusion device 10 may be resilient to being dropped, such as withstanding a 1500 g force with a 0.5 msec half-sine pulse duration (although other levels of impact resistance may be used). The infusion pump 10 will not be damaged by normal chemicals it may encounter: soap, insulin, suntan lotion, alcohol, betadine, Comet cleanser, 409 cleaner, Windex, Joy dish soap, 25% bleach mixture.

Preferred embodiments will utilize a cylindrical Li/MnO₂ primary battery.

| Part Number | Manufacturer |
| --- | --- |
| PX28L (1406LC NEDA/ANSI: IEC) | Duracell |

Alternative embodiments may use multiple batteries, or batteries having different chemical compositions or characteristics. For instance, embodiments may use silver-oxide based batteries, such as Energizer 357 batteries, mercury oxide, or other lithium chemistries. Further embodiments may include rechargeable batteries using either a DC powerport, induction, solar cells, or the like, for recharging.

Figure 13:
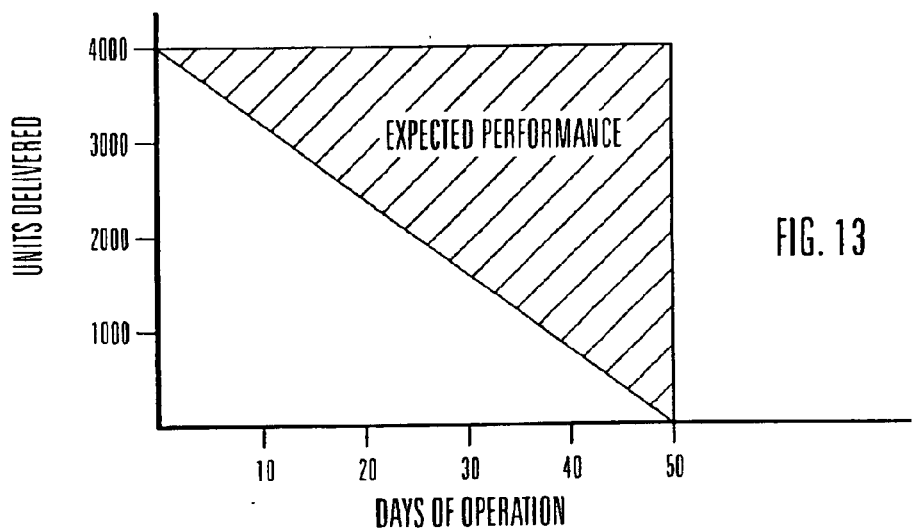
FIG. 13 is a graph showing units delivered versus expected days of operation on a set of batteries.

Preferably, the external infusion device 10 will report a low battery condition at a battery voltage of 4.2 volts with a 1.0 milliamp load. The absolute maximum current that may be delivered by the battery will be less than 60 milliamps for a maximum of 10 seconds. To maximize battery life, each delivery of 0.1 unit of insulin will consume less than 0.025 millijoules of battery energy. The average continuous battery current will not exceed 65 uA, excluding charging for insulin delivery. Preferably, the external infusion device 10 will indicate relative battery longevity. This information can be conveyed in a concept similar to a cellular phone's battery status indicator. FIG. 13 illustrates expected battery performance in days of operation versus units of medication delivered.

FIG. 14 illustrates a table of typical factory default values used by an external infusion device 10. Alternative embodiments, may use other default values with the selection being dependent on the types of medication or fluid to be infused.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An external infusion device for infusion of a liquid into a body a user from a reservoir, the external infusion device comprising:
    a drive mechanism to operatively couple with a reservoir to infuse a liquid into a body;
    a housing adapted for use on an exterior of the body, wherein the housing is sized to contain at least a portion of the reservoir, wherein the drive mechanism is at least partially contained within the housing, wherein the drive mechanism operatively couples with the at least a portion of the reservoir within the housing, and wherein the housing is sized to fit in a clothing pocket;
    a processor coupled to the housing;
    an audible alarm to provide primarily audible indications and which is operatively coupled to the processor to provide an audible alarm indication; and
    a separate vibration alarm configured to provide primarily tactile indications and to provide at least some agitation to the fluid in the reservoir and that is operatively coupled to the processor to provide a vibration alarm indication, wherein the user commands the procesor to activate one or more of the audible alarm and vibration alarm independently of the other alarm such that the user determines that the alarms are given as either audible alarm indications, tactile alarm indications or a combination of audible and tactile alarm indications.

2. An external infusion device according to claim 1, wherein the vibration alarm is also used to agitate the fluid in the reservoir in between successive delivery periods of the fluid by the external infusion device.

3. An external infusion device according to claim 1, wherein the vibration alarm is also used to agitate the fluid in the reservoir during delivery of the fluid by the external infusion device.

4. An external infusion device according to claim 1, wherein the housing is further adapted to be worn on a belt.

5. An external infusion device according to claim 1, wherein the housing is further adapted to be worn under clothing.

6. An external infusion device according to claim 1, wherein the housing is sized to allow for concealment under clothing in a generally unobtrusive manner.

7. An external infusion device according to claim 1, wherein the housing is further adapted to be worn against the skin.

8. An external infusion device according to claim 1, wherein the housing is further sized to be contained in the pocket.

9. An external infusion device according to claim 1, wherein the housing is further sized to be held within the pocket.

10. An external infusion device according to claim 1, wherein the vibration alarm provides one or more tactile sensations to the user in response to a low reservoir alert.

11. An external infusion device according to claim 1, wherein the vibration alarm provides one or more tactile sensations to the user in response to a communication from a remote commander.

12. An external infusion device according to claim 1, further including an input device coupled to the processor and the housing, wherein the vibration alarm provides one or more tactile sensations to the user in response to entry of one or more commands by the user utilizing the input device to change one or more operations of the external infusion device.

13. An external infusion device according to claim 1, wherein the vibration alarm provides one or more tactile sensations to the user during a period that the infusion device in a suspended mode.

14. An external infusion device according to claim 1, wherein the user selects to activate both the audible alarm and the vibration alarm together to provide the alarm.

15. An external infusion device for infusion of insulin into a body of a user from a reservoir, the external infusion device comprising:
a drive mechanism to operatively couple with a reservoir to infuse insulin into a body of the user;
a housing adapted for use on an exterior of the body of the user, wherein the housing is sized to contain at least a portion of the reservoir, wherein the drive mechanism is at least partially contained within the housing, wherein the drive mechanism operatively couples with the at least a portion of the reservoir within the housing, and wherein the infusion device housing is capable of being concealed from view on the user;
a processor;
an audible alarm to provide primarily audible indications and that is operatively coupled to the processor to provide an audible alarm indication; and
a separate vibration alarm to provide primarily tactile indications and to provide at least some agitation to the fluid in the reservoir and that is operatively coupled to the processor to provide a vibration alarm indication,
wherein the user selects to activate one or more of the audible alarm and vibration alarm such that the user determines which one or more alarms will be used to provide the user with notice of an alarm;
a display used in conjunction with the selected one or more alarms to provide visual information about the alarm; and
an input interface operatively coupled to the processor to allow the user to interface with the processor to control the alarm in the external infusion device.

16. An external infusion device according to claim 15, wherein the selected one or more alarms provide the alarm as either audible alarm indications or tactile alarm indications, and wherein this is provided with the visual information about the alarm.

17. An external infusion device according to claim 15, wherein the selected one or more alarms provide the alarm as a combination of audible and tactile alarm indications, and wherein this is provided with the visual information about the alarm.

18. An external infusion device according to claim 15, wherein the display provides the visual information to identify the alarm.

19. An external infusion device according to claim 15, wherein the display provides the visual information as at least one icon to identify the alarm.

20. An external infusion device according to claim 15, wherein the input interface is a keyboard.

21. An external infusion device according to claim 15, wherein the input interface is a remote commander.

22. An external infusion device according to claim 15, wherein the selected alarm is the audible alarm, and wherein the audible alarm escalates in volume.

23. An external infusion device according to claim 15, wherein the selected alarm is the vibration alarm, and wherein the tactile alarm indications increase in frequency.

24. An external infusion device according to claim 15, further comprising a transmitter to provide a signal representing the alarm, and wherein the transmitter transmits the signal to a remote location.

25. An external infusion device according to claim 24, wherein the signal is provided to a remote location through a relay.

26. An external infusion device according to claim 15, wherein the alarm is a programmable reminder to determine if additional boluses are needed at a later time after a meal.

27. An external infusion device according to claim 26, wherein the programmable reminder is to check blood glucose levels.

28. An external infusion device according to claim 15, wherein the alarm is a programmable reminder to determine if additional corrections are needed at a later time after a meal.

29. An external infusion device according to claim 28, wherein the programmable reminder is to check blood glucose levels.

30. An external infusion device according to claim 15, wherein the alarm is a settable alarm clock.

31. An external infusion device according to claim 30, wherein the alarm clock is used to remind the user to check blood glucose levels.

32. An external infusion device according to claim 30, wherein the alarm clock is used to remind the user to inject insulin.

33. An external infusion device according to claim 15, wherein the alarm is a no bolus should be given indication.

34. Au external infusion device according to claim 15, wherein the alarm is a low blood glucose level indication.

35. An external infusion device according to claim 15, wherein the alarm is a check blood glucose level indication.

36. An external infusion device according to claim 15, wherein the alarm is a lock-out period indication.

37. An external infusion device according to claim 15, wherein the alarm is a low reservoir indication.

38. An external infusion device according to claim 15, wherein the alarm is a suspend mode indication.

39. An external infusion device according to claim 15, wherein the housing is further adapted to be worn on a belt.

40. An external infusion device according to claim 15, wherein the housing is further adapted to be worn under clothing.

41. An external infusion device according to claim 15, wherein the housing is sized to allow for concealment under clothing in a generally unobtrusive manner.

42. An external infusion device according to claim 15, wherein the housing is further adapted to be worn against the skin.

43. An external infusion device according to claim 15, wherein the housing is further sized to be contained in the pocket.

44. An external infusion device according to claim 15, wherein the housing is further sized to be held within the pocket.

* * * * *